United States Patent [19]
Stanton et al.

[11] Patent Number: 5,807,552
[45] Date of Patent: Sep. 15, 1998

[54] COMPOSITIONS FOR CONFERRING IMMUNOGENICITY TO A SUBSTANCE AND USES THEREOF

[75] Inventors: G. John Stanton, Texas City; Thomas K. Hughes, Jr.; Eric M. Smith, both of Galveston, all of Tex.

[73] Assignee: Board of Regents, The University of Texas System, Austin, Tex.

[21] Appl. No.: 511,662

[22] Filed: Aug. 4, 1995

[51] Int. Cl.$^6$ .................................................. A61K 39/21
[52] U.S. Cl. ...................... 424/188.1; 424/184.1; 424/186.1; 530/324; 530/333; 530/826; 514/2; 514/12; 514/934; 535/5; 535/974
[58] Field of Search ................... 530/324–331, 530/333, 334, 826; 435/5, 974; 424/184.1, 186.1, 188.1; 514/2, 12–19, 934

[56] References Cited

U.S. PATENT DOCUMENTS

| | | | |
|---|---|---|---|
| 3,791,932 | 2/1974 | Schuurs et al. | 195/103.5 |
| 3,949,064 | 4/1976 | Bornstein et al. | 424/1 |
| 4,174,384 | 11/1979 | Ullman et al. | 424/8 |
| 4,578,770 | 3/1986 | Mitani | 364/571 |
| 4,596,792 | 6/1986 | Vyas | 514/21 |
| 4,599,230 | 7/1986 | Milich et al. | 424/89 |
| 4,599,231 | 7/1986 | Milich et al. | 424/89 |
| 4,601,903 | 7/1986 | Frasch | 424/92 |
| 4,608,251 | 8/1986 | Mia | 424/85 |
| 5,077,195 | 12/1991 | Blalock et al. | 435/6 |
| 5,229,490 | 7/1993 | Tam | 530/324 |

OTHER PUBLICATIONS

International Search Report dated Oct. 29, 1996 (UTFG:162P).

Blalock and Smith, "Hydropathic Anti-Complementarity of Amino Acids Based on the Genetic Code," *Biochemical and Biophysical Research Communications*, 121(1):203–207, May 1984.

Bost et al., "Similarity Between the Corticotropin (ACTH) Receptor and a Peptide encoded by an RNA That is Complementary to ACTH mRNA," *Proc Natl Acad Sci, USA*, 82:1372–1375, March 1985.

Chang and Meienhofer, "Solid–Phase Peptide Synthesis Using Mild Base Cleavage of $N^\alpha$-Fluorenylmethyloxycarbonylamino Acids, Exemplified by a Synthesis of Dihydrosomatostatin," *Int J Peptide Protein Res*, 11:246–249, 1978.

Goodman, "Immunogenicity & Antigenic Specificity," *In:Basic Human Immunology*, Stites, M.D. and Terr, M.D. (eds), Chapter 8, pp. 101–108, Appleton & Lange, Norwalk, Connecticut/San Mateo, CA., 1991.

Guillet et al., "Immunological Self, Nonself Discrimination," *Science*, 235:865–870, Feb. 1987.

Hale et al., "T Cell Multideterminant Regions in the Human Immunodeficiency Virus Envelope: Toward Overcoming the Problem of Major Histocompatibility Complex Restriction," *International Immunology*, 1(4):409–415, 1989.

Kyte and Doolittle, "A Simple Method for Displaying the Hydropathic Character of a Protein," *Journal of Molecular Biology*, 157:105–132, 1982.

R. B. Merrifield, "Solid Phase Peptide Synthesis: The Synthesis of a Tetrapeptide," *Journal of the American Chemical Society*, 85(14):2149–2154, July 1963.

Sette et al., "Structural Analysis of Peptides Capable of Binding to More Than One Ia Antigen," *Journal of Immunology*, 142(1):35–40, Jan. 1989.

James P. Tam, "Synthetic Peptide Vaccine Design: Synthesis and Properties of a High–Density Multiple Antigenic Peptide System," *Proc Nat Acad Sci, USA*, 85:5409–5413, Aug. 1988.

*Primary Examiner*—Donald E. Adams
*Assistant Examiner*—Jeffrey Stucker
*Attorney, Agent, or Firm*—Arnold, White & Durkee

[57] ABSTRACT

A multimer of monomers non-covalently held together by interactive peptide linkers is provided for the enhancement of the immunogenicity of a substance. These multimers are useful for stimulating or suppressing the immune system, detecting the presence of antibodies, bypassing MHC restriction in an animal, the effective presentation of antigen, suppressing autoimmune disease, inducing cytokine production, adsorption, treating a defective immune system and for use as an adjuvant.

13 Claims, 12 Drawing Sheets

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

Ser  Arg  Ala  Val  Thr  Ala  Ala  His  Ser  Glu  Ile
   1                 5                              10

( 2 ) INFORMATION FOR SEQ ID NO:2:

( i ) SEQUENCE CHARACTERISTICS:
      ( A ) LENGTH: 13 amino acids
      ( B ) TYPE: amino acid (C) STRANDEDNESS: single
        (D) TOPOLOGY: linear (i i) MOLECULE TYPE: peptide (x i) SEQUENCE DESCRIPTION: SEQ ID NO:2:

His Glu Asp Ile Ile Ser Leu Trp Asp Gln Ser Leu Arg
    1               5                   10

(2) INFORMATION FOR SEQ ID NO:3:

(i) SEQUENCE CHARACTERISTICS:
        (A) LENGTH: 11 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:3:

Ser Glu Ala Ile Ile His Val Leu His Ser Arg
    1               5                   10

(2) INFORMATION FOR SEQ ID NO:4:

(i) SEQUENCE CHARACTERISTICS:
        (A) LENGTH: 11 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:4:

Ala Leu Asp His Ser Gly Arg Val Arg Glu Thr
    1               5                   10

(2) INFORMATION FOR SEQ ID NO:5:

(i) SEQUENCE CHARACTERISTICS:
        (A) LENGTH: 11 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:5:

Arg Leu Ser Tyr Asn Val Asp Gln Met Arg Ala
    1               5                   10

(2) INFORMATION FOR SEQ ID NO:6:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:6:

Leu Lys Ile His Ala Gln Ile Glu Val Ser Val Ala
    1               5                   10

(2) INFORMATION FOR SEQ ID NO:7:

(i) SEQUENCE CHARACTERISTICS:
        (A) LENGTH: 12 amino acids
        (B) TYPE: amino acid ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Ala  Asn  Ile  Tyr  Ala  Glu  Ile  Asn  Ser  Tyr  Ile  Arg
1                  5                            10
```

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Asp  Val  Asn  Ala  Tyr  Leu  Asn  Leu  Arg  Phe  His  Tyr
1                  5                            10
```

( 2 ) INFORMATION FOR SEQ ID NO:9:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Gly  Leu  Gln  Phe  His  Val  Lys  Leu  Tyr  Gly  Glu  Ala
1                  5                            10
```

( 2 ) INFORMATION FOR SEQ ID NO:10:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Gly  Leu  Gln  Phe  His  Val  Lys  Leu  Tyr  Gly  Glu  Ala
1                  5                            10
```

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Leu  Arg  Phe  His  Tyr
1                  5
```

( 2 ) INFORMATION FOR SEQ ID NO:12:

( i ) SEQUENCE CHARACTERISTICS:
        ( A ) LENGTH: 4 amino acids
        ( B ) TYPE: amino acid -continued ( C ) STRANDEDNESS: single
( D ) TOPOLOGY: linear ( i i ) MOLECULE TYPE: peptide ( x i ) SEQUENCE DESCRIPTION: SEQ ID NO:12:

Gly Leu Gln Phe
1

COMPOSITIONS FOR CONFERRING IMMUNOGENICITY TO A SUBSTANCE AND USES THEREOF

FIELD OF THE INVENTION

The present invention relates to the field of immunology and to the enhancement of the immunogenicity of a substance. A new composition of matter is provided, a multimer of monomers non-covalently held together by interactive peptide linkers. These multimers are useful for stimulating or suppressing the immune system, detecting the presence of antibodies, bypassing MHC restriction in an animal, effective presentation of antigen, suppressing autoimmune disease, inducing cytokine production, adsorption, treating a defective immune system and for use as an adjuvant.

BACKGROUND OF THE INVENTION

Immunogenicity refers to the ability of a substance to induce a detectable immune response (humoral and/or cellular) when introduced into an animal. Such substances are called "immunogens." Antigenicity refers to the ability of a substance to bind to an antibody that is induced by exposure to an immunogen. Such substances are called antigens. Substances having a low molecular weight, such as drugs and antibiotics, are non-immunogenic, however, when coupled to an immunogenic protein, will induce antibodies having specificity for the low molecular weight substance. The terms "epitope" and "antigenic determinant" refer to the part of the antigen that is bound by antibody or T cell receptor.

Proteins are the most potent immunogens, but polysaccharides, synthetic polypeptides, and other synthetic polymers such as polyvinylpyrrolidone are immunogenic under certain conditions. For a general discussion of immunogenicity, a chapter authored by Goodman (1991) is incorporated by reference herein.

Immunogenicity is not an inherent property of a molecule but is dependent on experimental conditions. These conditions include the particular immunogen, the route of immunization, the host being immunized, and the sensitivity of the detection methods. Factors that confer immunogenicity on molecules are complex and incompletely understood, but certain conditions must be satisfied in order for a molecule to be immunogenic (Goodman, 1991). Those conditions include "foreignness", molecular size, chemical complexity, the genetic constitution of the animal, and the method of administration.

Foreignness

The immune system normally discriminates between "self" and "nonself," so that only molecules that are foreign to the animal are immunogenic.

Molecular Size

Small molecules such as amino acids or monosaccharides are not usually immunogenic, and it is generally accepted that a certain minimum size is necessary for immunogenicity. However, there is no specific size threshold below which all substances are inert and above which all are active. In a few instances, substances with molecular weights of less than 1000 have proved to be immunogenic, but as a general rule, molecules smaller than molecular weight 10,000 are only weakly immunogenic or not immunogenic at all. The most potent immunogens are macromolecular proteins with molecular weights greater than 100,000.

Chemical Complexity

A molecule must possess a certain degree of chemical complexity to be immunogenic. For example, synthetic polypeptides having repeating units of a single amino acid are poor immunogens regardless of size, whereas copolymers of 2 or 3 amino acids may be active. It is difficult to establish a definite threshold, and the general rule is that immunogenicity increases with structural complexity. Aromatic amino acids tend to contribute more to immunogenicity than non-aromatic residues. For example, relatively simple random polypeptides containing tyrosine are better antigens than the same polymers without tyrosine.

Genetic Constitution of the Animal

The ability to respond to a particular immunogen is a function of the way the immune response is controlled genetically. It has been known for some time that pure polysaccharides are immunogenic when injected into mice and humans but not when injected into guinea pigs. Further, strain 2 guinea pigs respond readily in an easily detectable manner to poly-L-lysine, whereas strain 13 guinea pigs do not. The ability to respond is inherited as an autosomal dominant trait.

Method of Immunogen Administration

Whether an immunogen will induce an immune response depends on the dose and the mode of administration. A quantity of immunogen that is ineffective when injected intravenously may evoke a copious antibody response if injected subcutaneously in adjuvant. In general, once the threshold is exceeded, increasing doses lead to increasing, but less than proportionate, responses. However, excessive doses may not only fail to stimulate antibody formation; they can also establish a state of specific unresponsiveness or tolerance.

Immunogenicity can be enhanced if the immunogen is mixed with substances termed adjuvants. Adjuvants function as follows: (1) by prolonging retention of the immunogen; (2) by increasing effective immunogen size, (3) by stimulating the influx of populations of macrophages and/or lymphocytes, or (4) by inducing certain cytokines. The most potent adjuvant for use in experimental animals is Freund's complete adjuvant (FCA), a water-in-oil emulsion containing killed mycobacteria. The adjuvant effect of FCA is aided by the provision of a depot for the immunogen and stimulation of macrophages and certain lymphocytes, but its very strong inflammatory effect precludes its use in humans. A muramyl dipeptide constituent of mycobacterial cell walls has also been found to possess adjuvant activity. The most widely used adjuvant in humans is a suspension of aluminum hydroxide on which the immunogen is adsorbed (alum precipitate). This adjuvant increases the effective particle size of the immunogen, promoting its presentation to lymphocytes.

When examined empirically, the amino acid residue sequences of peptides known to bind to major histocompatibility complex (MHC) binding sites, (Guillet et al., 1987; Sette et al., 1989; Hale et al., 1989), have a striking consistency of pattern of alternating hydrophilic and hydrophobic amino acid sequences separated occasionally by more neutral amino acids. The precise roles of alternating hydrophobic and hydrophilic amino acids in this or any protein binding system are unknown.

One method of preparing higher molecular weight peptides for use in vaccines has been published by Tam et al. (1988). In this method, a multimeric peptide antigen was chemically synthesized by covalently binding epitope subunits to amino groups of lysine cores. Eight to sixteen peptides could be incorporated into multimers using this method. The multimers were immunogenic in some mice but not others; and some, but not all, of the antibodies produced reacted with the native protein. There was a high probability that these multimers would denature. In fact, the aggregated forms were more useful in antibody ELISA assays.

Two promising new approaches to vaccine development have emerged in the modern era of biomedical technology. One is the cloning of genes coding for important surface proteins of infectious agents, with production of large quantities of the desired protein by microorganisms transfected with the gene. A recombinant vaccine containing the major surface protein of the hepatitis B virus has recently been approved and marketed (Goodman, 1991).

The other approach is the chemical synthesis of short peptides from known sequences of proteins from infectious organisms. The peptides may be linked to carriers, thereby becoming "synthetic immunogens." This approach is predicated on the assumption that antibodies induced to short peptides of the order of 6–15 amino acids will react with the homologous sequences in the native proteins. In fact, it has been shown that antibodies to peptides representing sequences from the exposed surfaces of folded proteins, where they are accessible to antibody, do react with the native molecules, although the affinities of binding may be lower than with the peptides themselves. These findings offer promise for the manufacture of synthetic vaccines that are based on the hapten-carrier principle for use in human and animal prophylaxis. However, an important consideration is that immunologic memory in the response to hapten-carrier conjugates is directed primarily at the carrier, which bears the immunogenic determinants. Since the carriers are different in the synthetic vaccine and the native protein from which the peptide came, an encounter with the infectious agent following immunization with the synthetic vaccine should elicit little or no memory against the peptide and its carrier. Although sufficiently high antibody titers raised by the vaccine could provide substantial protection even without memory, this does represent a serious limitation for this type of vaccine. Due to limitations such as these, those of skill in this art have tried new approaches to enhancing the immunogenicity of substances for the preparation of synthetic vaccines.

SUMMARY OF THE INVENTION

The present invention provides linkers having amino acid sequences of alternating hydrophobic and hydrophilic amino acid(s) for attachment to the amino and carboxy terminal ends of a peptide to form a monomer. The linkers bind strongly to each other in a non-covalent manner, thereby, multimerizing the monomer and conferring immunogenicity to the multimerized peptide.

The present invention provides the synthesis of protein molecules with repeating active sites for any particular biological activity. The multimers of the present invention are effective because: 1) the subunits are not held together by covalent bonds but by natural amino acid side chain interactions, thus allowing their tertiary conformation to be more flexible and natural; 2) they allow a greater number and variety of immunogens, antigens, epitopes or ligands to be easily incorporated into them; 3) since the linkers are not covalently bound, their flexibility allows a greater chance for the incorporated immunogen, antigen, epitope or ligand to have high affinity interaction with its appropriate receptor; and 4) the binding of the monomers in the system of the present invention does not require the use of potentially toxic chemicals or a large amount of manipulation that can lead to protein denaturation. The present non-covalently linked multimeric peptides are also sufficiently soluble to use in vitro or in vivo as immunogen, antigen, epitope or receptor binders and/or stimulators. In addition, the present non-covalently linked multimeric peptides have the potential of being produced by recombinant technology or used directly as virally or, bacterially, expressed vaccines.

The present invention provides a non-covalently interlinked multimer comprising monomers (A)-Ag-(a) and (B)-Ag-(b). In this muiltimer, Ag is preferably an HP-6 epitope but may be a peptide having from about 5 to 30 amino acids. A, a, B, and b are independently peptide linkers of about 3 to 12 amino acids, where peptide linker A has binding affinity for peptide linker b, and peptide linker a has binding affinity for peptide linker B due to a pattern of alternating hydrophilic and hydrophobic amino acids or groups of amino acids. The multimer herein defined preferably has immunogenicity.

In a preferred embodiment of the present invention, A and B are the same linker and a and b are the same linker. The pattern of hydrophilic and hydrophobic amino acids may be one of singly alternating hydrophilic and hydrophobic amino acids or may be one of alternating groups of 2 or 3 amino acids. The peptide linkers may have spacer amino acids.

In a particularly preferred embodiment of the present invention, A and a are selected from the group consisting of S1-L and S1-R, S2-L and S2-R, M1-L and M1-R, M2-L and M2-R, S20-L and S20-R, and S22-L and S22-R; and B and b are selected from the group consisting of S1-L and S1-R, S2-L and S2-R, M1-L and M1-R, M2-L and M2-R, S20-L and S20-R, and S22-L and S22-R.

The present invention also provides for a monomer comprising the structure (A)-Ag-(a) wherein Ag is an HP-6 epitope; and A and a are independently peptide linkers of about 3 to 12 amino acids. In this monomer, peptide linker A has non-covalent binding affinity for peptide linker a due to a pattern of alternating hydrophilic and hydrophobic amino acids or groups of amino acids.

A further embodiment of the present invention is a set of peptide linkers for enhancing immunogenicity of a substance when covalently linked with the substance. The set of linkers comprises a first and a second peptide linker, each linker having between about 3 to 12 amino acids and having a sequence of alternating hydrophilic and hydrophobic amino acids or groups of amino acids. The first peptide linker has non-covalent binding affinity for the second peptide linker due to the sequence of alternating hydrophilic and hydrophobic amino acids or groups of amino acids.

The present invention also provides a non-covalently interlinked multimer made by a process comprising the step of incubating a monomer, (A)-Ag-(a), with a monomer, (B)-Ag-(b), under conditions facilitating peptide interactions to form a non-covalently interlinked multimer. In this monomer, Ag is an HP-6 epitope; and A, a, B, and b are independently peptide linkers of about 3 to 12 amino acids; wherein peptide linker A has non-covalent binding affinity for peptide linker b and peptide linker a has non-covalent binding affinity for peptide linker B due to a pattern of alternating hydrophilic and hydrophobic amino acids or groups of amino acids. In this process, the conditions facilitate dissolution of the monomers in a physiologically acceptable aqueous solvent.

The term "peptide linker A having binding affinity for peptide linker b" means that upon contacting linker A with linker b, for example, under appropriate conditions of ionic strength, temperature, pH and the like, specific interaction will occur. The term "binding affinity" means that the linkers interact with an association constant of at least $10^4$. The interaction may occur due to specific electrostatic, hydrophobic, entropic or other interaction of alternating hydrophobic and hydrophilic amino acid residues of linker A with an alternating pattern of hydrophobic and hydrophilic amino acid residues of linker b, to form a stable complex under the conditions effective to promote the interaction. The interaction may alter the three dimensional conformation of either or both linkers involved in the interaction and it may also alter the function or activity of either or both linkers involved in the interaction. For example, the interaction of linker A with linker b when linker A and b are part of a monomer as defined herein enhances immunological properties of the resultant monomer.

A method of producing a non-covalently interlinked multimer comprising the step of incubating a monomer, (A)-Ag-(a), with a monomer, (B)-Ag-(b), under conditions facilitating peptide interactions to form a non-covalently interlinked multimer is also an aspect of the present invention. In this method, Ag, A, a, B, and b are as described hereinabove.

The Linkers

Linkers may be made up of: a) natural amino acid sequences that bind to natural amino acid sequences of receptors or vice versa and/or to themselves, b) custom designed amino acid sequences that bind to other custom designed amino acid sequences or to themselves because their amino acid sequences are designed to allow optimal interaction of their hydrophilic, hydrophobic and neutral amino acid side chains, c) amino acid sequences that bind in natural proteins to give such proteins their characteristic tertiary structure, and/or d) any combinations of these. Amino acid sequences in linkers could be manipulated to increase or decrease binding affinity and/or enhance presentation of the antigenic epitope. For example, spacer amino acids, such as neutral amino acids may be included in the linkers to allow for rotational flexibility and maximal interaction of a hydrophobic amino acid side chain on one linker with a hydrophobic amino acid on another linker and similarly, allow maximal interaction of a hydrophilic amino acid side chain of one linker with a hydrophilic amino acid side chain on another linker. Thus, more stable or less stable multimers could be made with desired degrees of flexibility for binding to receptors.

Linkers are preferably at least 3 amino acids long and not more than about 12 amino acids long. The linkers have a pattern of alternating hydrophobic and hydrophilic amino acids. A preferable pattern is singly alternating hydrophobic and hydrophilic amino acids, however, alternating sets of 2 or 3 amino acids are also contemplated. These alternating sets of hydrophobic and hydrophilic amino acids may be interrupted by a spacer amino acid as described above to allow maximal interaction of amino acid side chains. A linker preferably has at least one hydrophilic and one hydrophobic amino acid.

Modification and changes may be made in the structure of the amino acid linkers and still obtain a multimer having like or otherwise desirable characteristics. For example, certain amino acids may be substituted for other amino acids in a linker without appreciable loss of interactive binding capacity. Since it is the interactive capacity and nature of an amino acid sequence that defines the linker's functional activity, certain amino acid sequences may be chosen (or, of course, its underlying DNA coding sequence) and nevertheless obtain a linker with like or even countervailing properties (e.g., antagonistic v. agonistic). It is thus contemplated by the inventors that various changes may be made in the sequence of a linker (or underlying DNA) without appreciable loss of its ability to multimerize.

Substitution of like amino acids can be made on the basis of hydrophilicity, particularly where the biological functional equivalent linker thereby constructed is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent peptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginie and lysine; glutamate and aspartate; serine and threonine; glutamine and asparagine; and valine, leucine and isoleucine.

For purposes of the present invention, hydrophobic amino acids include alanine, valine, isoleucine, leucine, tryptophan and phenylalanine; polar amino acids include histidine, asparagine, glutamine, cysteine, methionine, tyrosine, threonine and serine; positively changed amino acids include lysine and arginine; negatively charged amino acids include aspartic acid and glutamic acid and a neutral amino acid is glycine. Although not tested, proline was not considered desirable in the linkers of the present invention since proline promotes a turn in the secondary structure of a peptide.

Two designations for amino acids are used interchangeably throughout this application, as is common practice in the art. Alanine=Ala (A); Arginine=Arg (R); Aspartate=Asp (D); Asparagine=Asn (N); Cysteine=Cys (C); Glutamate= Glu (E); Glutamine=Gln (Q); Glycine=Gly (G); Histidine= His (H); Isoleucine=Ile (I); Leucine=Leu (L); Lysine=Lys (K); Methionine=Met (M); Phenylalanine=Phe (F); Proline= Pro (P); Serine=Ser (S); Threonine=Thr (T); Tryptophan =Trp (W); Tyrosine=Tyr (Y); Valine=Val (V).

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

For a particular multimer, amino acids in the linker sequences next to the desired immunogen, antigen, epitope or ligand may be altered somewhat to get optimum activity. In the present examples, the region closest to the agent included more neutral amino acids rather than strongly hydrophilic or hydrophobic amino acids. These neutral amino acids are referred to as spacer amino acids.

The Central Component of the Monomer

The central component of the monomer is most readily envisioned as a peptide although various other types of central units may be attached to the novel peptide linker sequences as described herein. When a preferred central component is a peptide, it may be immunogenic, i.e., comprise desired immunologically active epitopes or combinations of epitopes. These immunoactive epitopes may be, for example: 1) immunosuppressive epitopes or antigenic epitopes, depending upon the particular end being sought; or 2) in some cases an activator, stimulator or blocker of a desired biological activity, e.g., a hormone, a hormone receptor or bioactive substance of another type such as activators, stimulators or blockers of any biologic activity in which defined ligands and receptors are required to interact. When the central component is immunologically active, it should have sufficient size to define the immunological activity, e.g., when it is an antigenic epitope (Ag), it would bind to antibodies. A preferred central component is an HIV HP-6 epitope that reacts with anti-HP-6 antibody, and having from about 5 to about 30 amino acids. In particular, a 13 amino acid HP-6 epitope is most preferred, although one of skill in the art would realize in light of this disclosure that the epitope may be 6, 7, 8, 9, 10, 11, 12, 14, 15, 16, 17, 18, 19, 20, 22, 24, 26 or 28 amino acids long. These non-covalently bound multimers may be used in kits, columns, etc., or enzyme linked immunosorbent (ELISA) assays where the identification, isolation, concentration, or assay of a desired antibody, cell type, ligand, receptor, etc., is required or useful. They may also be used as stabilizers and protectors of labile proteins or other molecules.

The present invention allows the production of potent, synthetic, high molecular weight, multivalent vaccines made up of large numbers, or types of antigenic epitopes. These include glycosylated epitopes or epitopes developed from conserved sequences, from any organism or cell, e.g., viral, bacterial, parasitic, cancer, etc. These same multimers could also contain ligands that will stimulate signalling molecules, such as hormones, lymphokines and/or cytokines that will enhance the immune response locally where the multimers are transported and/or processed. These same multimers could also contain ligands that would bind to FcγR (receptor) on macrophages and dendritic antigen presenting cells, thus greatly enhancing their antigenicity. Targeting of FcγR cells could also be made via monoclonal IgG antibody bound to multimer linkers.

The synthesis of monomers that include a peptide within their sequence is readily achieved using conventional peptide synthetic techniques such as the solid phase method (e.g., through the use of commercially available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of immunogenic activity. However, where extended aqueous storage is contemplated, it will generally be desirable to include agents including buffers such as Tris-HCl or phosphate buffers to maintain a pH of 7.0 to 7.5. Moreover, it may be desirable to include agents which will inhibit microbial growth, such as sodium azide or merthiolate. For extended storage in an aqueous state, it will be desirable to store the solutions at 4° C., or more preferably, frozen. Of course, where the peptide(s) are stored in a lyophilized or powdered state, they may be stored virtually indefinitely, e.g., in metered aliquots that may be rehydrated with a predetermined amount of water (preferably distilled) or buffer prior to use.

The present invention also provides a method of altering the immune system of a subject comprising the steps of i) identifying a subject in need of immune system alteration; and ii) administering to the subject a pharmaceutically effective amount of a non-covalently interlinked multimer of the present invention. In a preferred embodiment of this method, altering the immune system is stimulating the immune system, the non-covalently interlinked multimer may be S1 or S2, for example, and cytokine production is induced in the subject. The cytokine may be IFN-τ, IL-1 or INF-α. In a further preferred embodiment of the present invention, altering the immune system is suppressing the immune system. This suppression may result from the induction of cytokine IL-b10. Altering the immune system may include bypassing MHC restriction in the subject.

Vaccines

The present invention contemplates vaccines for use in both active and passive immunization embodiments. The multimers of the present invention possess tertiary structure and have valence and, therefore, are excellent candidates for providing immune protection for humans or animals against any organism, cancer, or autoimmune disease. Further, multimers made according to the present invention could be used for desensitizing hyperimmune individuals, for bypassing major histocompatibility restriction, for crosslinking B cell receptors or FcγR receptors, or for better antigen presentation (e.g., linkers may be capable of being cleaved by intracellular enzymes).

Immunogenic multimers, proposed to be suitable for use as a vaccine, may be prepared in a manner disclosed herein. Preferably, the immunogenic multimers are extensively dialyzed to remove undesired small molecular weight molecules and/or lyophilized for more ready formulation into a desired vehicle.

The preparation of vaccines that contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables, either as liquid solutions or suspensions. Solid forms, suitable for solution or suspension in liquid prior to injection, may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

To use multimerized peptides that contain immunogenic peptides as the basis for a human vaccine, the toxicity should be reduced or eliminated. Multimers of the present invention are not mitogenic for naive T lymphocytes and cannot be considered as superantigens. Superantigens are known to induce apoptosis or toxicity and therefore would be considered as harmful components of a vaccine.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides: such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10–95% of active ingredient, preferably 25–70%.

The multimers may be formulated into the vaccine as neutral or salt forms. Pharmaceutically acceptable salts, include the acid addition salts (formed with the free amino groups of the peptide) and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the weight of the host.

The multimers of the present invention are particularly advantageous for use as a vaccine because the valence provided by the multimerization decreases the need for an adjuvant. However, further methods of achieving adjuvant effect for the vaccine include, but are not limited to, use of agents such as aluminum hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 70° to 101° C. for 30 second to 2 minute periods respectively. Aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the multimer. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

Further Uses of Multimers

Multimers of the present invention are contemplated to be useful in a variety of ways, in addition to their effect on the immune system as exemplified herein. Additional uses that are envisioned include; the activation or blocking of receptors, the activation of cytokine and/or lymphokine responses, provision of stability for labile molecules, as a carrier, coating or adsorption of toxic drugs or toxins in any environment including treatment of overdoses of toxic drugs, for detection of antibodies in a biological sample such as ELISA assays, the synthesis of simple enzymes, protein purification procedures, and antibody capture technology.

A method for detecting anti-HIV antibody in a sample is also an aspect of the present invention. The method comprises the steps of: i) obtaining a sample suspected of having an anti-HIV antibody; ii) contacting the sample with an anti-HIV antibody-binding amount of a non-covalently interlinked multimer of claim 1; and iii) measuring binding of the multimer to the sample. The presence of anti-HIV antibody in the sample is determined from the binding. Preferably, the sample is human blood. In a preferred embodiment of this method, the multimer is S1 or S2. The measuring step is carried out using a detectably labeled antibody specific for the anti-HIV antibody and the detectably labeled antibody is labelled with a fluorescent tag, a radiolabel or an enzyme.

The present invention also provides a method of producing an antibody having specific binding affinity for the non-covalently linked multimer of the present invention in an animal. This method comprises the steps of obtaining an animal capable of producing antibody and injecting into the animal the non-covalently interlinked multimer. Preferably, the antibody is recovered from biological fluid of the animal.

Immunoassay

The present invention, in still another aspect, defines an immunoassay for the detection of an antibody specific for a multimerized peptide in a biological sample. In one particular embodiment, the immunoassay comprises; preparing a multimerized peptide, incubating the multimerized peptide with the biological sample for a sufficient time to permit binding between multimerized peptide and antibody present in said biological sample, and determining the presence of bound antibody by contacting the incubate of the multimer and antibody with a detectably labeled antibody specific for the anti-multimer antibody, wherein the presence of anti-multimer antibody in the biological sample is detectable as a measure of the detectably labeled antibody from the biological sample.

By way of example, the detectably labeled antibody may be labeled with any of a variety of detectable molecular labeling tags, such as; an enzyme-linked (alkaline phosphatase) antibody, a fluorescent-tagged antibody, or a radio-labelled antibody.

A test kit for the detection of HIV antibody in a biological sample is also an aspect of the present invention. The kit comprises in packaged combination: i) a carrier means adapted to receive a plurality of container means in close confinement therewith, ii) a first container means including a non-covalently interlinked multimer of the present invention, iii) a second container means including a quantity of an unlabelled antibody having specific binding affinity for the multimer, and iv) a third container means including a quantity of a detectably labelled antibody having specific binding affinity for the unlabelled antibody. Preferably, the detectably labelled antibody is an enzyme linked antibody, a fluorescent tagged antibody, or a radiolabeled antibody. In a preferred embodiment of the test kit, the detectably labelled antibody is an enzyme linked antibody, and said pack further includes a fourth container means including a quantity of a substrate for the enzyme sufficient to produce a visually detectable product.

Immunodetection Kits

In still further embodiments, the present invention concerns immunodetection methods and associated kits. It is proposed that the multimers of the present invention may be employed to detect antibodies having reactivity therewith. In general, these methods will include first obtaining a sample suspected of containing such an antibody, contacting the sample with a multimer in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot, dot blot, indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For diagnostic purposes, it is proposed that virtually any sample suspected of comprising the antibody sought to be detected, as the case may be, may be employed. Exemplary samples include clinical samples obtained from a patient such as blood or serum samples, ear swabs, sputum samples, middle ear fluid, vaginal, or urine samples may be employed. Furthermore, it is contemplated that such embodiments may have application to non-clinical samples, such as in the titering of antigen or antibody samples, in the selection of hybridomas, in the production of absorbent columns, kits where any kind of high affinity specific binding is required, and the like.

In related embodiments, the present invention contemplates the preparation of kits that may be employed to detect the presence of antibodies or specific binding agents in a sample. Generally speaking, kits in accordance with the present invention will include a suitable multimer or antibody directed against such a multimer, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container means will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

BRIEF DESCRIPTION OF THE DRAWINGS

FIG. 6A shows multimeric M1 and multimeric M2 separated on a 7.5% non-denaturing electrophoretic gel. FIG. 6B shows monomers M1 and M2 in the presence of 2% SDS and separated on an 18% polyacrylamide gel.

FIG. 1 shows TNF-α induction by treatment of naive human leukocytes with multimers as numbered for FIG. 9.

Figure 1:
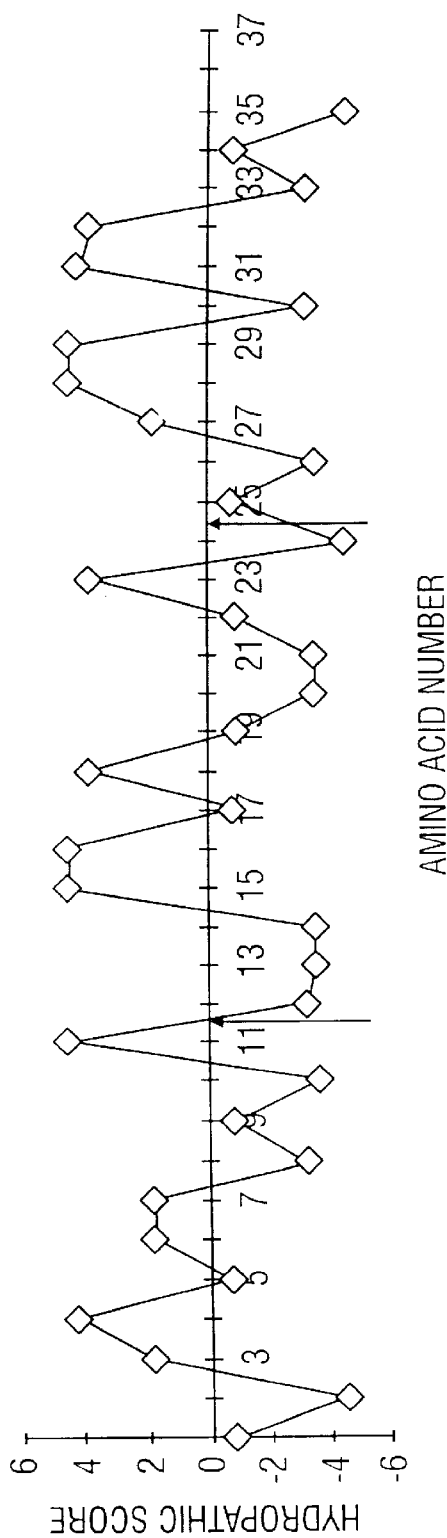
FIG. 1 graphically illustrates the hydropathic score of the amino acids of monomer M1. Amino acids 1–11 of peptide M1 are the left linker region with the sequence: Ser-Arg-Ala-Val-Thr-Ala-Ala-His-Ser-Glu-Ile, SEQ ID NO: 1. Amino acids 12–24 of peptide M1 are the HIV antigen, HP-6, with the sequence: His-Glu-Asp-Ile-Ile-Ser-Leu-Trp-Asp-Gln-Ser-Leu-Arg, SEQ ID NO:2. Amino acids 25–35 of peptide M1 are the right linker region with sequence: Ser-Glu-Ala-Ile-Ile-His-Val-Leu-His-Ser-Arg, SEQ ID NO:3.
Figure 2:
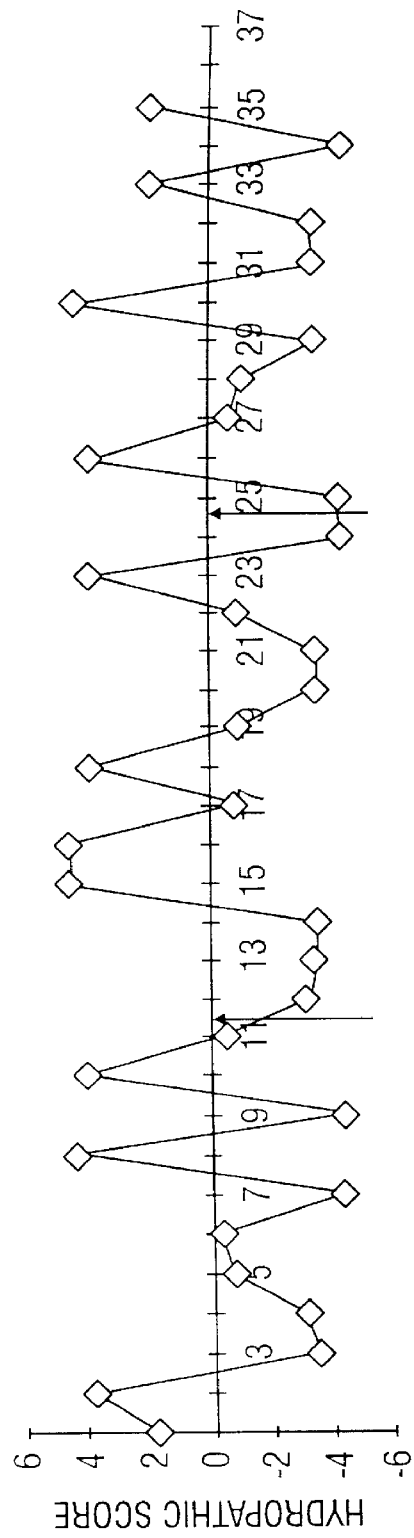
FIG. 2 graphically illustrates the hydropathic score of the amino acids of monomer M2. Amino acids 1–11 of peptide M2 are the left linker region with the sequence: Ala-Leu-Asp-His-Ser-Gly-Arg-Val-Arg-Glu-Thr, SEQ ID NO:4. Amino acids 12–24 of peptide M2 are the HIV antigen, HP-6, with the sequence: His-Glu-Asp-Ile-Ile-Ser-Leu-Trp-Asp-Gln-Ser-Leu-Arg, SEQ ID NO:2. Amino acids 25–35 of peptide M2 are the right linker region with sequence: Arg-Leu-Ser-Tyr-Asn-Val-Asp-Gln-Met-Arg-Ala, SEQ ID NO:5.
Figure 3:
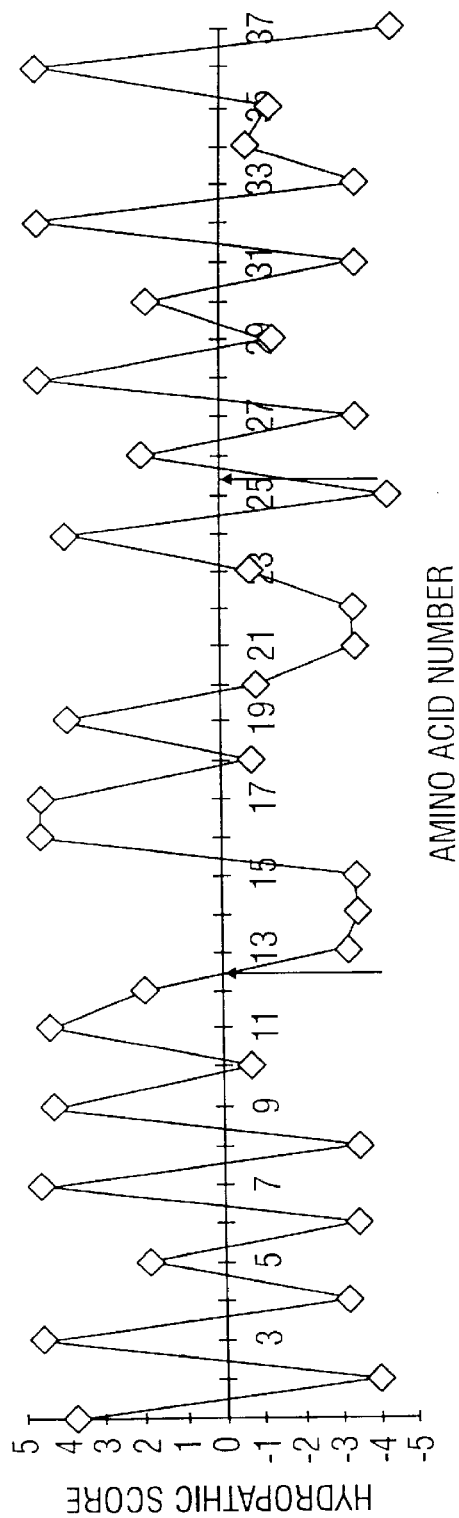
FIG. 3 graphically illustrates the hydropathic score of the amino acids of monomer S1. Amino acids 1–12 of peptide S1 are the left linker region with the sequence: Leu-Lys-Ile-His-Ala-Gln-Ile-Glu-Val-Ser-Val-Ala, SEQ ID NO:6. Amino acids 13–25 of peptide S1 are the HIV antigen, HP-6, with the sequence: His-Glu-Asp-Ile-Ile-Ser-Leu-Trp-Asp-Gln-Ser-Leu-Arg, SEQ ID NO:2. Amino acids 26–37 of peptide S1 are the right linker region with sequence: Ala-Asn-Ile-Tyr-Ala-Glu-Ile-Asn-Ser-Tyr-Ile-Arg, SEQ ID NO:7.
Figure 4:
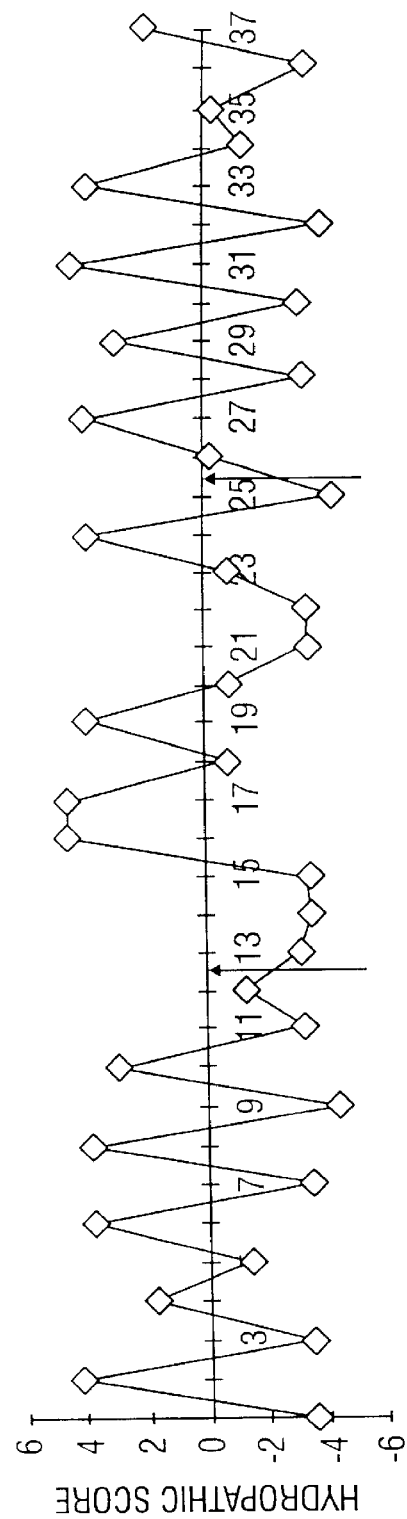
FIG. 4 graphically illustrates the hydropathic score of the amino acids of monomer S2. Amino acids 1–12 of peptide S2 are the left linker region with the sequence: Asp-Val-Asn-Ala-Tyr-Leu-Asn-Leu-Arg-Phe-His-Tyr, SEQ ID NO:8. Amino acids 13–25 of peptide S2 are the HIV antigen, HP-6, with the sequence: His-Glu-Asp-Ile-Ile-Ser-Leu-Trp-Asp-Gln-Ser-Leu-Arg, SEQ ID NO:2. Amino acids 26–37 of peptide S2 are the right linker region with sequence: Gly-Leu-Gln-Phe-His-Val-Lys-Leu-Tyr-Gly-Glu-Ala, SEQ ID NO:9.

DETAILED DESCRIPTION OF THE PREFERRED EMBODIMENTS

The present invention provides custom designed multimeric peptides, the monomers of such multimeric peptides being bound to each other by non-covalent interactions. By incorporating eight or ten medium to strongly hydrophobic and hydrophilic amino acids in a binding sequence or selecting natural amino acid sequences that contained similar arrangements of amino acids, the present inventors have linked central units such as peptides, using natural binding forces, into large, stable multimers. Further, the linker sequences were added on both sides of an antigenic epitope greatly enhancing the activity of the epitope.

The present invention teaches the design and synthesis of non-covalently linked large peptide multimers that have many of the properties of biologically active natural proteins with tertiary structure. In addition, these multimers have a considerable advantage over natural proteins used as vaccines, receptor stimulators or blockers, because they have incorporated into them copies of various biologically active high affinity epitopes and/or ligands that can activate or block immune or other important biologic receptors. Multiple copies of epitopes or ligands in the same molecule result in multimers with valence. Valence is necessary for establishing immune responses with memory. It is generally known that epitopes in their natural high molecular weight forms, i.e., proteins, are considerably more avid and active than the isolated small molecular weight peptides themselves. Therefore, because multimers of the present invention are high molecular weight structures, the activity of the repeated copies of epitopes or ligands incorporated into them is enhanced. Biologic studies described herein indicate that the affinities, avidities and stabilities are sufficient to induce morphological changes and cytokine production in naive human leukocytes and an immune response in naive mice. The multimers of the present invention may be eluted from single high molecular weight bands on polyacrylamide gels and reisolated as equally high molecular weight bands on another gel. This is an indication that they are very stable.

No uses of amino acid linker sequences to bind peptides to form biologically active, non-covalently bound, large molecular weight peptide molecules or multimers with valence, i.e., repeated copies of epitopes or ligands, were found in extensive literature and patent searches of peptide uses for vaccines. U.S. Pat. No. 5,077,195 entitled "POLYPEPTIDES COMPLEMENTARY TO PEPTIDE OR PROTEINS HAVING AN AMINO ACID SEQUENCE OR NUCLEOTIDE CODING SEQUENCE AT LEAST PARTIALLY KNOWN AND METHODS OF DESIGN THEREFOR" concerns the ability of two peptides to bind to each other, one synthesized according to the linear information on the−strand of DNA that is complementary to the transcribed+strand of DNA or amino acid sequences derived from it, and the other synthesized from information on the+strand. The patent enumerated ways that complementary peptides can be used to induce antibodies useful for the isolation of receptors, modulate the immune response by induction of anti-idiotypic antibodies, bind to molecules for their isolation, or identification, and to determine the amino acid sequence of a protein.

No suggestion is made in the literature of using complementary linker peptides to make high molecular weight avid multimeric vaccines, nor of the fact that multimeric proteins can be made without any information about a sequence of codons derived from the genetic or amino acid sequences derived therefrom. Complementary sequences could theoretically be used as linkers in the present system, because they can be selected to contain significant numbers of alternating hydrophobic and hydrophilic amino acid sequences depending on which+strand sequences are selected. However, the experiments described herein indicate that the mechanisms given for complementary peptide binding based on the genetic code actually are not involved in the linkage observed in the present invention, especially since 8 of the linkers were picked and/or designed to contain very few complementary amino acids. In addition, when the binding abilities of peptides that could bind by complementary sequences (M1 and M2, S1 and S2) were investigated by polyacrylamide gels electrophoresis, the polyacrylamide gel profiles obtained were the same as for those peptides that did not contain complementary sequences (M1 alone, M2 alone, S1 alone, and S2 alone) (see Examples). This finding indicates that, in spite of the design, the binding in all cases was consistent with mechanisms of binding associated with a certain amount of alternating hydrophobic and hydrophilic amino acid sequences and not complementary binding as defined by U.S. Pat. No. 5,077,195.

The advantages that the present synthetic multimeric vaccines would have over presently used live virus and killed virus or subunit vaccines include: 1) they would be more stable and not be as risky as live virus vaccines; 2) single or numerous optimally selected, repeating epitopes, could be incorporated into high molecular weight multimers with tertiary confirmation, while live virus or killed vaccines only contain one or two epitopes of a particular type per molecule; 3) the repeating units give the vaccine molecules valence that would greatly enhance their ability to induce memory cells for long term immunity, thus lessening or eliminating the need for multiple injections; 4) they would be much easier and cheaper to produce, therefore, high effective concentrations of multimeric vaccines could be given, possibly without the use of adjuvants; 5) multiple epitopes from different virus variants could be incorporated into the same molecule, thus broadening the immune response to cover infections in which antigenic variants develop; and 6) the same multimers could contain antigenic determinants as well as ligands that stimulate lymphokine and/or cytokine responses that enhance immune responses.

It was unexpected that peptides containing linkers with only one complementary pair of amino acids (in the sense of complementarity described in U.S. Pat. No. 5,077,195) out of 11 would link to each other, or 3 out of 11 when only two of them are adjacent. It was also a surprise that peptides containing a chimeric linker taken from different amino acid sequences of ovalbumin/influenza hemagglutinin (OVA/HA) and a linker from myoglobin, both of which bind to MHC product $1A^d$ of mice would bind to themselves in multimeric forms (see Examples 1 and 2).

Monomers with linkers complementary to the amino acid sequences OVA/HA and myoglobin would not have been predicted to bind to themselves in a similar fashion (see Examples 1 and 2). Monomers made from the present linkers, in which an antigenic epitope of HIV has been sandwiched, would not have been expected to have biological activity in naive cell cultures of mice and humans and to be immunogenic in mice. Thus, the multimeric peptides of the present invention have in vitro biologic activity in leukocyte cell cultures and in vivo activity in mice (see Examples). Another interesting advantage of the present invention is that epitopes have adjuvant effects from the linkers.

Depending on the size, structural characteristics and ability to induce cytokine by particular molecular weight multimers, they could be either immunogenic (IL-1B, TNFα, IFNγ) or immunosuppressive (IL-10). Studies with leukocytes are consistent with this, since different forms and numbers of activated cells appear in cultures based on the multimer or combination of multimers used to stimulate them (e.g., increased or decreased incidence of large mononuclear type cells and branched elongated cells, such as dendritic cells, both of which play active roles in controlling the immune response). In addition, some multimers decrease the cell culture effects of others when they are added in combinations, suggesting activation or suppression of leukocyte or immune responses.

Smaller molecular weight multimers containing epitopes to autoimmune antigens are expected to be immunosuppressive because of the inverse relationship between size and immunogenicity of many antigens. Thus, the use of multimers containing these epitopes for potential therapy against autoimmune disease is feasible.

The multimers may be able to bypass immune histocompatibility complex restriction, thus broadening the immune response to any restricted antigen, due to the ability to manipulate and produce a variety of forms of the multimers containing a variety of epitopes.

The present invention also provides for the construction of multimeric vaccines containing conformational epitopes derived from the tertiary structure of antigenic proteins due to the ability to manipulate and produce a variety of forms of the multimers. Such epitopes are strongly antigenic.

Due to the ability to manipulate and produce a variety of forms of the multimers containing multiple epitopes (valence), it is also possible to link B-cell receptors with antigenic epitopes. Thus, it is possible to induce immune memory cells and also use B-cells as antigen presenting cells. This capability would enhance the potential formation of memory cells, thus decreasing the requirement of yearly vaccination required for effective use of many vaccines.

The present invention provides for multimers containing target amino acid sequences for enzymes involved in intracellular antigen processing because of the ability to manipulate and produce a variety of forms of the multimers. These target sequences would be located where the linkers are attached to peptide epitopes. Thus, enhanced cellular processing and presentation of antigen may be possible.

The multimers of the present invention can be used as stimulators, binders or blockers of any biologic activity or protein molecule where ligands and receptors are required to interact because of the tertiary structure and potential high affinity of the multimers.

The use of multimers containing specific epitopes for antibody capture, assays, or purification procedures is feasible. Such a method would allow isolation, purification, and characterization of antibodies to specific epitopes that may be highly important for the protection of animals and humans against virus, bacterial, parasitic, cancer, and the like; thus enabling refined design of epitopes to be included in vaccines.

The present invention also provides for the production of synthetic vaccines that are less likely to induce autoimmune disease due to the ability to make linkers that could mimic normal beta sheet amino acid sequences of proteins found in an animal species, or sequences that are not found in a species' proteins.

Due to the way the linkers bind, it would be possible to produce multimers with biological activity by placing the epitope(s) or ligand(s) at the end of a linker or sequence of linkers. Thus, epitopes or ligands could be made to extend from the multimers. These could be more effective in binding to certain receptors for activating or blocking purposes.

Due to their tertiary structure and potential high avidity and affinity, multimers containing a desired ligand could be used as improved binders of any protein molecule, or part of a protein molecule, in which a ligand and its receptor can interact, e.g., in kits, columns, ELISA assays or the like, where the identification, isolation, concentration, or assay of a desired antibody, cell type, ligand, receptor, or the like is required or useful. Multimers of the present invention may stabilize, protect, and/or carry labile proteins or adsorb toxic molecules.

The present invention also envisions the production of synthetic enzymes out of multimers because of the ability to manipulate and produce a variety of forms of the multimers. The multimers of the present invention may also be used in injectable, oral, anal, vaginal and/or nasal vaccines, and the like.

Further applications for the immunoenhancing linker systems of the present invention are: (1) enhanced immunogenicity of conserved epitopes of HIV or other organisms, (2) induction of immunogenicity for desired amino acid sequences on the surface of HIV or other organisms, (3) enhanced immunogenicity of tumor antigens, (4) desensitization for allergens, (5) cell migration, and (6) wound healing (induction of cytokines, growth factor, etc. for enhanced healing).

Further applications for immunosuppressive linker systems would be: 1) improvement in treatment of autoimmune disease, and 2) prevention of apoptosis in treatment of early AIDS.

Multimers may be attached to multimers containing linked foreign epitopes, e.g., tumor antigen, virus antigens such as mumps virus, and the like, to virus infected cells or cancer cells, thus making them much more immunogenic and/or susceptible to killing by specific antibodies or cytotoxic cells directed toward the epitope. Attachment could be accomplished by: a) linking multimers to monoclonal antibodies that react with specific ligands on the cells; b) linking multimers to protein receptors, or ligands that will bind to a specific unique receptor on a cell; c) incorporating specific parts of ligands or receptors into multimers that bind to their counterparts.

Since the monomers that make up the multimers can bind under natural conditions, it may be possible to produce and use multimers in recombinant technology including: a) the production of multimeric vaccines; or b) the use of recombinant vectors producing multimers as vaccines. The DNA sequence of any monomer can be easily determined from the genetic code and these sequences are sufficiently small to put several into the same vector, thus it may be possible to express multimers in vectors such as plasmids or phage using bacteria or viruses as hosts, for example.

Since multimers bind in a variety of ways, the production of multimers that can bind to labile proteins, vaccines, hormones, and the like, and make them more stable, protect them, or serve as carrier proteins is envisioned by the present invention. Further, multimers that can specifically block undesired nonspecific binding, e.g., binding to protein isolation and purification equipment, containers, contaminating proteins, and the like, are envisioned by the present invention. Multimers that can absorb or neutralize toxic materials in blood, e.g., drugs or by-products from pharmaceutical agents are also envisioned.

Due to the ability to manipulate and produce a variety of forms of the multimers containing a variety of ligands, it is envisioned to incorporate ligands into multimers that would facilitate their entry into cells, e.g., virus components. Such ligands incorporated along with enhancer or blocker ligands could help control intracellular processes including processes that lead to tumorigenicity, apoptosis, and the like. The ability of the multimers themselves to cause autoimmune disease should be very low because the amino acid sequences used can be chosen to exclude any known vertebrate sequence.

The following examples are meant to illustrate particular preferred embodiments of the present invention, in addition to a description of the general approach involved. These examples are not meant to limit the scope of the claimed invention but merely to illustrate the preferred embodiments.

EXAMPLE 1

DESIGN OF LINKER-Antigen-LINKER MONOMERS

Monomers were designed and prepared that had amino acid linker sequences are bound to the N- and C-terminal ends of a peptide antigenic epitope. Thus, a monomer is designated linker-antigen-linker. A linker sequence is an amino acid sequence that would non-covalently bind to an amino acid sequence on the end of another monomer or possibly to itself due to a pattern of alternating hydrophobic and hydrophilic amino acid residues. In the present example, the antigen is a peptide and is covalently bound to the linkers, i.e., the antigen is sandwiched in the middle of a set of linkers.

In the following illustration, the linker AAAAAAA was designed to link with linker bbbbbbbb and not with linker aaaaaaaa; and the linker aaaaaaaa was designed to link with BBBBBBBB and not AAAAAAAA. In this model, the letters represent specific amino acid sequences that were designed to link, and Ag stands for an antigenic antigen or ligand.

Unexpectedly, results also indicated that linkers of a monomer also bound to each other as shown in this illustration:

Specific amino acid linkers made by the present inventors and incorporated into monomers are listed in Table 1. Those linkers positioned to the left or at the amino terminal end of the antigen are designated L, e.g., M1-L; and those linkers positioned to the right or at the carboxy terminal end of the antigen are designated R, e.g., M1-R. The amino acids are designated as hydrophobic, Φ; polar, δ; charged, +/−; or neutral, 0.

For purposes of the present invention, hydrophobic amino acids include alanine, valine, isoleucine, leucine, tryptophan and phenylalanine; polar amino acids include histidine, asparagine, glutamine, cysteine, methionine, tyrosine, threonine and serine; positively changed amino acids include lysine and arginine; negatively charged amino acids include aspartic acid and glutamic acid and a neutral amino acid is glycine. Proline is not desirable in the linkers of the present invention since proline promotes a turn in the secondary structure of a peptide.

TABLE 1

Amino Acid Sequence of Linkers Showing Patterns of Hydropathy[1]

| | | | | | | | | | | | | |
|---|---|---|---|---|---|---|---|---|---|---|---|---|
| M1-L | Ser δ | Arg + | Ala Φ | Val Φ | Thr δ | Ala Φ | Ala Φ | His δ | Ser δ | Glu – | Ile Φ | SEQ ID NO: 1 |
| M1-R | Ser δ | Glu – | Ala Φ | Ile Φ | Ile δ | His Φ | Val Φ | Leu Φ | His δ | Ser δ | Arg + | SEQ ID NO: 3 |
| M2-L | Ala Φ | Leu Φ | Asp – | His δ | Ser δ | Gly 0 | Arg + | Val Φ | Arg + | Glu – | Thr δ | SEQ ID NO: 4 |
| M2-R | Arg + | Leu Φ | Ser δ | Tyr δ | Asn δ | Val Φ | Asp – | Gln δ | Met δ | Arg + | Ala Φ | SEQ ID NO: 5 |
| S1-L | Leu Φ | Lys + | Ile Φ | His δ | Ala Φ | Gln δ | Ile Φ | Glu – | Val Φ | Ser δ | Val Φ | Ala Φ SEQ ID NO: 6 |
| S1-R | Ala Φ | Asn δ | Ile Φ | Tyr δ | Ala Φ | Glu – | Ile Φ | Asn δ | Ser δ | Tyr δ | Ile Φ | Arg + SEQ ID NO: 7 |
| S2-L | Asp – | Val Φ | Asn δ | Ala Φ | Tyr δ | Leu Φ | Asn δ | Leu Φ | Arg + | Phe Φ | His δ | Tyr δ SEQ ID NO: 8 |
| S2-R | Gly 0 | Leu Φ | Gln δ | Phe Φ | His δ | Val Φ | Lys + | Leu Φ | Tyr δ | Gly 0 | Glu – | Ala Φ SEQ ID NO: 9 |
| S20-L | Arg + | Phe Φ | His δ | Tyr δ | | | | | | | | SEQ ID NO: 10 |
| S20-R | Gly 0 | Leu Φ | Gln δ | | | | | | | | | |
| S22-L | Leu Φ | Arg + | Phe Φ | His δ | Tyr δ | | | | | | | SEQ ID NO: 11 |
| S22-R | Gly 0 | Leu Φ | Gln δ | Phe Φ | | | | | | | | SEQ ID NO: 12 |

[1]L — left linker, R — right linker, Φ — hydrophobic amino acid, δ — polar amino acid, +/– — positively/negatively charged amino acid, 0 — neutral amino acid.

The linkers for monomer M1 (Table 1) were chosen from amino acid sequences determined by Sette et al. to bind strongly to mouse MHC IA$^d$ molecules. Thus, it was known that these sequences have an endogenous binding capacity and eight or nine hydrophobic and hydrophilic residues each. The 11 amino acid sequence chosen for the left linker (M1-L) contained essentially the same sequence as Sette's chimeric peptide OVA/HA 5.9 (OVA 324–334/HA 132–142), except that an arginine residue was substituted for glutamine at position 2. The amino acid sequence chosen for the right linker contained a myoglobin sequence. Since the linkers were made up of amino acid sequences from different proteins and since they both bound to MHC IA$^d$ molecules, it was thought highly unlikely that they would bind to each other. Thus, the M1 linkers were expected to fit the non-interacting selective criteria for left and right linkers on the same monomer.

The linkers on M2 (see Table 1) were designed to be complementary to the linkers on M1, using the Blalock et al. theory (Blalock et al., Bost et al.), (i.e., amino acid sequences consistent with the probable genetic code of the non-transcribed DNA strand) with the exception that, in the left linker, Asp was placed opposite of Ala in position 3 and Thr was placed opposite of Ile in position 11. These substitutions were made so that the linker would be somewhat more hydrophilic on the N-terminus and somewhat more neutral on the end attached to the antigen. Again the design of these monomers made it unlikely that the linker sequences on the N-and C-terminal ends of the monomer M2 would bind to each other.

Hydrophobic and hydrophilic binding between beta (β) sheet structures, and/or alpha (α) helix structures are very important for folding and stabilizing natural proteins. However, in most natural protein structures, usually only 2 to 4 alternating hydrophilic and hydrophobic residues are present in α helices or β sheets that can interact. Therefore, another pair of monomers, S1 and S2, were specifically designed to allow optimal interaction between hydrophobic and hydrophilic residues, i.e., in contrast to the M1 linkers, the left and right linker amino acid sequences of S1 and S2 were not based or selected from any known sequence of amino acids. In S1, an extended sequence pattern of alternating hydrophobic and hydrophilic amino acids was selected. The N- and C-terminal linker sequences of S1 and S2 (see Table 1) also were designed not to bind to each other according to the Blalock theory. Thus, of the 12 amino acids in each linker, no more than three were complementary, indicating that it would be highly unlikely that the monomer would bind to itself in a manner described by Blalock et al.

Specifically, monomers S1 and S2 were designed to contain linker sequences having alternating strong to intermediate hydrophobic and charged or polar hydrophilic amino acid residues (Table 1). Starting with the N-terminal amino acid of the left and right linkers, amino acids with strong to intermediate hydrophobic side chains were placed opposite amino acids with a comparable hydrophilic side chain to give an alternating pattern in the S1 versus S2 linkers. Thus, strongly hydrophobic amino acids in the linkers of the S1 peptide could bind with strongly hydrophobic amino acids in the S2 linkers and vise versa. The hydrophilic amino acids were similarly situated so they could bind with each other. More neutral or polar amino acids were placed at positions 10 and 34 of S1 and a neutral Gly at 26 and 35 of S2 to enable flexibility. One of skill in this art would realize in light of the present disclosure that the amino acids in the linker sequences next to the desired epitope or ligand may have to be altered to get optimum activity. It was expected that peptides having these amino acid sequence patterns would bind to each other or themselves in a fashion similar to parallel beta sheets. Thus, the alternating nature of the hydrophobic and hydrophilic amino acids in the left and right linkers of the same peptide would allow binding of the same peptides to each other to form multimers containing one type of monomer.

Two further monomers, S20 and S22, were synthesized to examine the minimum number of alternating hydrophobic and hydrophilic (or polar) amino acids needed in linkers to confer biological activity to a monomer of which the linkers are a part. Monomer S20 contained the HP-6 epitope (described below) sandwiched between linkers that contained one hydrophobic amino acid, and monomer S22 contained HP-6 sandwiched between linkers that contained two hydrophobic amino acids. Thus, S20 has one and S22 has two alternating hydrophobic amino acids at each end of the epitope.

The human immunodeficiency virus (HIV) T cell epitope, peptide HP-6, was selected from Hale et al. (1989) and incorporated into each monomer between the left and right linkers. This particular gp160 envelope epitope (residues 112–124) was chosen because it was immunogenic in H-$2^k$ haplotype mice but not in H-$2^d$ haplotype mice. Thus, it could be used to study the immunogenicity of multimers containing HP-6 in restricted H-$2^d$ mice. The sequence of HP-6 is:

His-Glu-Asp-Ile-Ile-Ser-Leu-Trp-Asp-Gln-Ser-Leu-Arg,
SEQ.ID.NO.2

The hydropathic patterns of the monomers M1, M2, S1, and S2 are shown in FIG. 1–FIG. 4.

The above-described peptides were synthesized by the solid phase method of Merrifield (1963) using an automatic peptide synthesizer, with standard t-butoxycarbonyl (t-Boc) chemistry that is well known to those skilled in this art in light of this disclosure. The amino acid composition and the sequence analysis of the synthesized peptides correspond to the expected compositions. The amino acid composition of the peptides was determined by amino acid analysis. The purity of the peptides was determined by sequence or HPLC.

EXAMPLE 2

GEL PROFILES OF MULTIMERS

To determine if the monomers would bind to themselves or to each other and form multimers, they were solubilized in 100 percent DMSO and diluted to 1.0 to 2.0 mg/ml with TRIS-HCl glycine buffer at pH 8.8. Aliquots (50 µl) of individual monomers and combinations of monomers were then subjected to non-denaturing polyacrylamide gel electrophoresis (PAGE) on 18 or 7.5 percent gels, pH 8.8, or to denaturing sodium dodecyl sulfate (SDS) PAGE. Following electrophoresis, the peptides in the bands of the gels were visualized with Coomassie blue and/or silver stains.

The results of two representative experiments on 18 percent non-denaturing gels (FIG. 5) showed that certain monomers bound to each other to form multimers that migrated as distinct bands. The sharpness and equity of distance between the bands indicated that the monomers had bound or complexed to form multimers in a very distinct, repetitive, and stable manner. If binding had been random, the multimers would have appeared as long gray smears. Each band represents a multimer with a different molecular weight. The precise molecular weights of the multimers are not defined because of the difficulty in determining the molecular weights of proteins electrophoresed in non-denaturing gels. However, it is apparent from the positions on the gels that the multimers have considerably higher molecular weights than the monomers since the monomers migrated close to the dye front when treated with 2% SDS and electrophoresed in a 7.5% non-denaturing gel (FIG. 6A) or subjected to denaturing SDS PAGE in an 18% gel (FIG. 6B). The broadness of the bands at the bottom of the denaturing gel indicate that, even under these conditions, some binding occurred that was stable. Importantly, these findings indicate that the multimers are made up of sequentially repeating monomers resulting in multimers with a gradient of different sizes. An estimation of a molecular weight for the smaller multimers is greater than about 15,000 since multimers M1, M2, S1, S2, M1+M2, and S1+S2 did not diffuse out of dialysis tubing having a $M_r$ cutoff size of 12,000 to 15,000.

Figure 5:
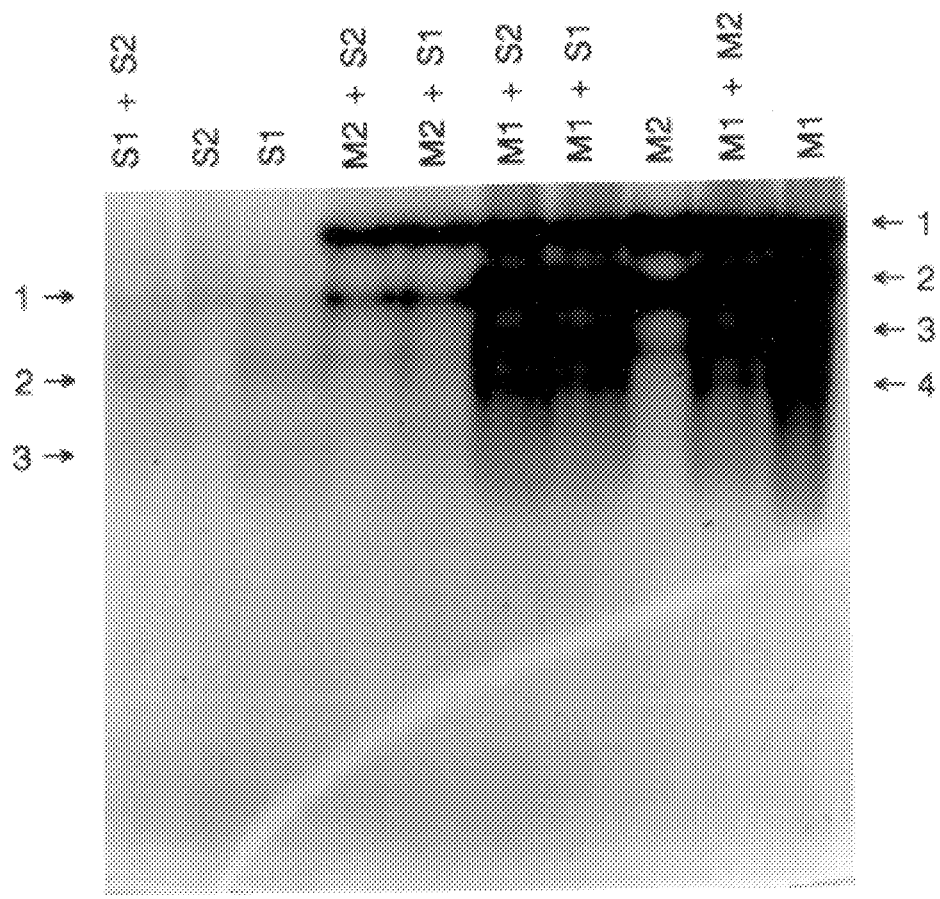
FIG. 5 shows multimeric bands after electrophoresis on an 18% polyacrylamide gel under non-denaturing conditions. Monomers M1, S1, M2, S2 and combinations thereof were tested.
Figures 6A, 6B:
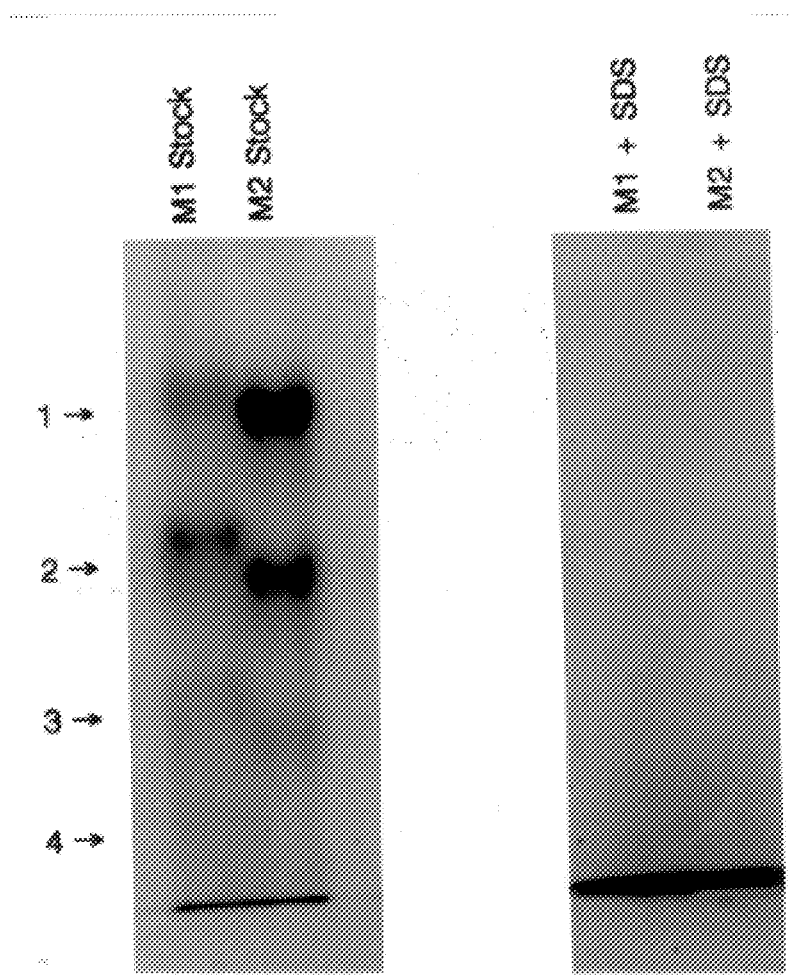
FIGS. 6A–B show gel electrophoretic patterns of multimeric M1 and Multimeric M2.

More specifically, it can be observed in FIG. 5, FIG. 6A and FIG. 6B that the M1 monomer complexed to form four bands of multimers while the M2 monomer formed three. Some intermediate random binding also occurred with M1, as indicated by the diffuse gray areas. It is possible that the M1 monomer is more likely to form higher molecular weight multimers. Although the two monomers differ considerably in their amino acid sequences (the linker sequences of the M2 peptide is the complement of M1 according to the Blalock et al. theory) the multimers of both essentially migrate the same. Thus, similar mechanisms of binding and formation of multimers are probably operating in both instances. When M1 and M2 were mixed and separated by electrophoresis, the pattern of migration of the multimers were the same as M1 by itself. Thus, it is presently not possible to determine whether M1 and M2 bound to each other. However, if they did bind, the banding pattern suggests that the mechanism of binding was similar to the binding of M1 and M2 to themselves. Thus, the binding is not consistent with a complementary type of "lock and key binding" as proposed by Blalock et al., since it is highly unlikely that monomers M1 and M2 would bind to themselves by "lock and key" type binding.

When M1 and M2 were mixed with S1 or S2 and separated by electrophoresis, the migration patterns were again the same as M1 or M2 alone. Thus, it is not possible to tell whether binding occurred between these monomers. Only slight binding appeared to occur with the S1, S2 and S1 plus S2 monomers, however, where bands can be observed, the patterns are the same as with the M1 and M2 monomers, again suggesting a similar mechanism of binding. When higher concentrations of S1 and S2 were mixed and separated by electrophoresis, the bands were much more distinct. Additionally, the S1 and S2 multimers do not stain well with the silver stain.

Taken together, the data indicate that whether individual multimers or any combination of multimers were electrophoresed on non-denaturing polyacrylamide gels, the molecular sizes observed were essentially the same. This data strongly indicate that the fundamental mechanism of formation of all the multimers is the same.

The actual length or minimum number of strongly hydrophobic or hydrophilic amino acids required to get stable binding and/or biological activity per linker is estimated as follows. Both linking and biological activity were observed for the M1 and M2 multimers as described in later Examples. Since these multimers have as few as two to three strongly hydrophobic or hydrophilic amino acid residues per linker that could interact with each other, these numbers approximate the minimum number of alternating strongly active amino acids required for binding and enhanced activity. The HIV epitope without linkers has no in vitro activity and very little, if any, in vivo activity.

To confirm the stability of the multimers in the bands and to assure that the multimers elutable from the different bands would remain stable, multimers of M1 and M2 were eluted from the precise areas of the gel and re-subjected to non-denaturing PAGE. The bands were resolved with Coomassie blue followed by silver stain. The results show that the multimers migrated to form single bands at the same relative positions as they were eluted from the first gel. None of the bands dissociated into lower band forms; indicating that the multimers are stable. Together, these data indicate that the eluted multimers are both stable and homogeneous and that the multimeric forms used to immunize mice or stimulate leukocyte cultures in the following Examples were of the same size as the ones eluted from the gels.

In summary, S1, S2, M1 and M2 monomers all can form distinct bands of similar types of multimers on gels. It appears that the monomers must bind together in several (3–4, depending on the linkers) thermodynamically stable conformations. Although the S monomers do not form distinct multimers on low percent gels, the distribution, i.e., size, of the multimers on the higher percentage gels are similar to the M multimers but more random. The differences between the two M and S multimers are that the S multimer stocks are much more active in the systems tested in the following Examples than the M multimer stocks. This is an advantage because these multimers could be used without extensive isolation procedures and, of course, could be incorporated into vectors for commercial, e.g., vaccine and other biological uses. The ability to form multimers of different sizes and possible conformations allows for diversity for optimizing presentation of ligands or epitopes.

EXAMPLE 3

IMMUNIZATION OF MICE

The present example provides data demonstrating that specific and general immune responses were elicited in mice due to injection of multimers of the present invention.

M2 multimers (containing HP-6) were eluted from the upper two bands of non-denaturing PAGE gels and studied to determine if they would differ from: 1) each other in their ability to stimulate immune responses in vivo, or 2) stock M2, which contains all the multimers, or 3) the HIV epitope alone. Specifically, female ICR outbred mice were inoculated subcutaneously at the base of the tail with the following samples: 50 μg of upper band (band 1 of FIG. 6A), lower band (band 2 of FIG. 6A), multimers, M2 dialyzed stock, or the HIV epitope. Each inoculum was thoroughly emulsified in Freund's complete adjuvant prior to injection. The amount of stimulation, indicated by $^3$H-thymidine incorporation into lymph node cells ($4 \times 10^6$/ml) prepared seven days after immunization and incubated for five days in the presence of the indicated stimulants, is shown in Table 2. Staphylococcal enterotoxin A (SEA), a specific T cell mitogen, was also used to stimulate cultured cells to determine if T cell activity had been generally stimulated.

TABLE 2

T Lymphocyte Stimulation Following Immunization of ICR Mice with Multimers[a]

| Lymph Node Cells Stimulated with: | Mice Immunized With: | | | |
|---|---|---|---|---|
| | M-2 Stock Dialyzed | HIV-epitope alone | M2-Band 1 | M2-Band 2 |
| Media | 1397 ± 283 | 1189 ± 433 | 771 ± 167 | 1844 ± 387 |
| SEA 0.2 μg/ml | 11243 ± 2405 | 5318 ± 732 | 9096 ± 2193 | 249396 ± 20925[b] |
| M-2 Stock Dialyzed | | | | |
| 8 μg/ml | 1611 ± 524 | 3498 ± 1743 | 5216 ± 2476[c] | 29682 ± 4277[b] |
| 4 μg/ml | 1511 ± 270 | 1456 ± 1328 | 2152 ± 209[b] | 24062 ± 6149 |
| 2 μg/ml | 3613 ± 228 | 861 ± 535 | 1912 ± 425 | 19135 ± 184 |
| 1 μg/ml | N.D. | N.D. | N.D. | 14168 ± 5828 |
| M-2 Band 1 | | | | |
| 8 μg/ml | 1059 ± 10 | 1113 ± 70 | 1097 ± 359[c] | 6264 ± 1276[b] |
| 4 μg/ml | 2664 ± 1143 | 697 ± 236 | 901 ± 28 | 8725 ± 1537 |
| 2 μg/ml | 2263 ± 713 | 499 ± 28 | 756 ± 151 | 7244 ± 2815 |
| 1 μg/ml | N.D. | N.D. | N.D. | 6979 ± 1276 |
| M-2 Band 2 | | | | |
| 8 μg/ml | 2457 ± 261 | 926 ± 262 | 1384 ± 96[c] | 13089 ± 424[b] |
| 4 μg/ml | 1992 ± 1150 | 640 ± 148 | 1011 ± 41 | 9746 ± 4460 |
| 2 μg/ml | 1535 ± 38 | 827 ± 51 | 749 ± 160 | 9391 ± 1932 |
| 1 μg/ml | N.D. | N.D. | N.D. | 6437 ± 1640 |
| HIV-epitope alone | | | | |
| 8 μg/ml | 786 ± 30 | 1493 ± 1109 | 5047 ± 3941 | 5863 ± 386[b] |
| 4 μg/ml | 1870 ± 199 | 714 ± 255 | 2114 ± 420[c] | 6523 ± 670 |
| 2 μg/ml | 1318 ± 690 | 1003 ± 680 | 1332 ± 95 | 4291 ± 389 |
| 1 μg/ml | N.D. | N.D. | N.D. | 4205 ± 540 |

[a] = cpm ± S.D., $^3$H-thymidine was added to cultures on day 4 and amounts incorporated in DNA counted on day 5.
[b] = Significant at the p = <0.05 level by the Student's t-test.
[c] = Significant at the p = 0.1 level The results indicate that immunization with the lower band (Band 2) multimer greatly enhanced the lymph node cell response to SEA as well as the response to the dialyzed M-2 stock, the upper band (Band 1) multimers, and to itself (P—<0.0001, 0.045 and 0.016, respectively, by Student's t test). Importantly, the response to the HIV-epitope alone was significant at the P=0.043 level.

In contrast, lymph node cells of mice immunized with the Band 1 multimers did not respond as significantly to Band 1 or Band 2 multimers (P=0.095). However, a significant response to SEA occurred (P=<0.05). No significant responses occurred when mice were immunized with the HIV epitope alone or dialyzed stock, which theoretically contains all the multimers. This observation is consistent with the findings of others that find animals immunized with peptides alone, or even peptides bound to carrier protein, often do not respond very strongly.

It is noteworthy that a significant response occurred to the HIV epitope alone when the Band 2 multimer was used as antigen (P=0.043), indicating that specific immunoactivation of lymph node cells, very likely T cells, to the HIV epitope occurred. The lymph node response to the HIV epitope in mice immunized with the Band 1 was marginally significant at the P=0.1 level; however, a good dose response occurred that, when statistically evaluated, should determine this response as significant. It presently has not been determined whether a specific immune response to the linker part of the M2 multimer occurred. It is possible that some or all of the positive stimulation responses to the dialyzed stock, Band 2 and Band 1 were specific for the HIV epitope and the degrees of differences observed were due to the various ways epitopes in the multimers were presented to the immune system and/or to the sensitized cells stimulated during culture. Thus, dialyzed stock containing numerous forms of the multimers was an excellent stimulator of lymph node cell cultures prepared from mice immunized with the Band 2 multimers, but a poor stimulator of the immune system when it was used as antigen.

Overall these studies indicate that multimers designed according to the present invention can be effectively used to stimulate specific and "general" immune responses, as indicated by the enhanced immune responses to the HIV epitopes present in multimers and to SEA.

The immunologic effects of the S1 and S2 multimers in mice have also been tested. Because of the inability to stain bands intensely on gels with these monomers, which also "sandwich" an HIV epitope, stock preparations were used to prepared from immunized mice by the counts incorporated into stimulated cultures from unimmunized mice. It can be observed that the S2 stock multimers, which contains all forms of the multimers, was highly immunogenic in ICR mice when compared to the other multimers and its own linkers (S2LL+RL). Stimulation by S1, which contains the HIV epitope but different linkers was twice as active as the other peptides used, indicating that the mice immunized with S2 had responded, at least in part, to the HIV epitope. This specificity is further indicated by the ability of HP-6, the HIV epitope alone, to stimulate the cultures from mice immunized with S2 compared to the HP-6 activity in cultured cells taken from mice immunized with HP-6 (HP-6 vs. HP-6). Unexpectedly, the linkers alone had activity even when mice had not been exposed to them, e.g., the S1 LL+RL. Stimulation by the M1 and M2 stock multimers was less than expected but at least equivalent to PPD which should be active because Freund's complete adjuvant was used in the immunizations. Overall the data suggest that the S2 stock multimers are highly immunogenic in ICR mice and that the responses are, at least in part, specific for the HIV epitope HP-6. The fact that some linkers are active in cultured lymph node cells from mice not previously exposed to them suggests that they have immunomodulatory effects themselves. Since the S1 stock multimers were not immunogenic in these mice, these multimers may be restricted in this strain of mouse or may be immunosuppressive.

Figure 8:
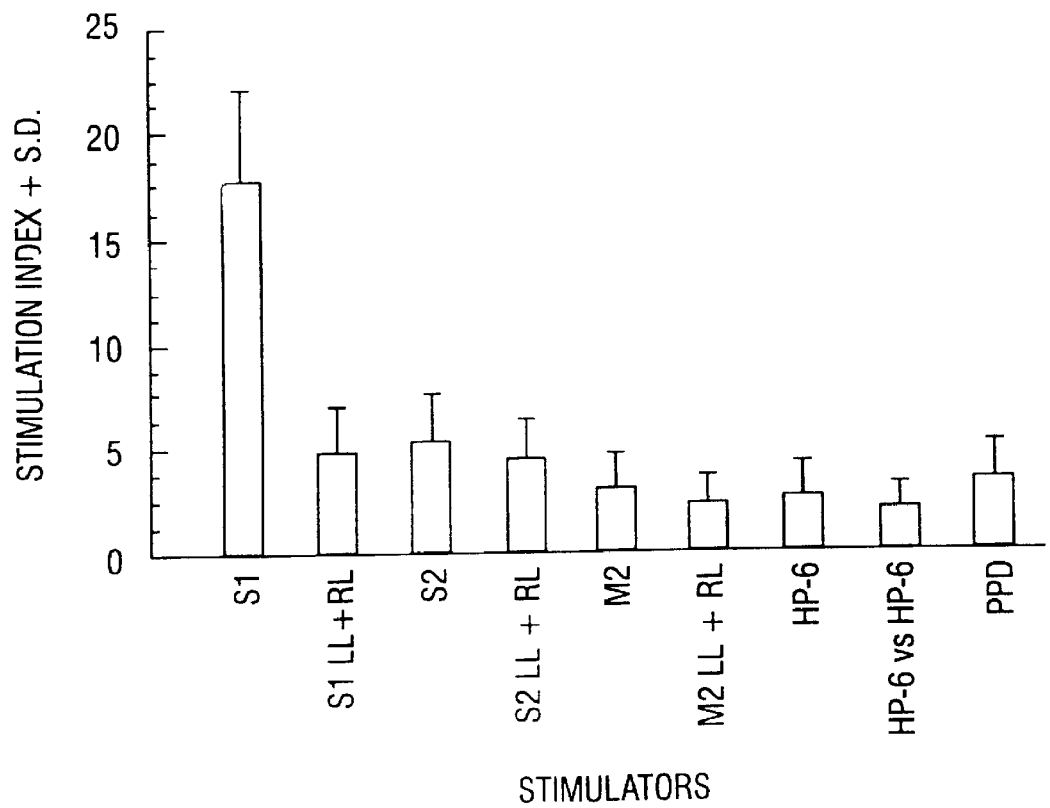
FIG. 8 shows the proliferative response of lymph node cells from S1 immunized BALB/c mice after exposure to the indicated stimulators.

FIG. 8 shows the proliferative responses and standard deviations of lymph node cells from BALB/c inbred mice. This strain of mouse was investigated because it had been reported that HP-6 was immunologically restricted in mice that had been immunized with gp160 envelope protein of HIV (Hale, et al.). Mice were immunized with S1 or S2 multimers and the lymph node cells stimulated as indicated. These mice could be immunized with the S1 stock but not the S2, possibly because S2 was immunosuppressive in these mice (Table 3).

TABLE 3

Immunosuppression of the Proliferative Response of Lymph Node Cells from Mice Immunized with the S2 Peptide and Stimulated by Media, PPD or SEA

| Mouse strain | Mice immunized with: | | | | | | | | |
|---|---|---|---|---|---|---|---|---|---|
| | S1 peptide + FCA[a] | | | S2 peptide + FCA | | | FCA alone | | |
| | Media | PPD[b] | SEA[c] | Media | PPD | SEA | Media | PPD | SEA |
| ICR | 8[d] | 6639 | 4660 | 34 | 11041 | 14333 | 16 | 1535 | 115 |
| BALB/c | 30 | 717 | 4346 | 6 | 24* | 53* | 10 | 209 | 1528 |
| C₃H | 21 | 1903 | 12333 | 9 | 253 | 8157 | 4 | 33 | 2567 |

[a] = Freunds complete adjuvant
[b] = Purified protein derivative of *M. tuberculosis*
[c] = Staphylococcal enterotoxin A (T cell mitogen)
[d] = Counts per minute
* = Significant suppression (p = <.001 by student test)

immunize groups of ICR, BALB/c and C3H mice. Immunizations, lymph node cell preparations, and stimulation assays were all performed as described in this Example.

Figure 7:
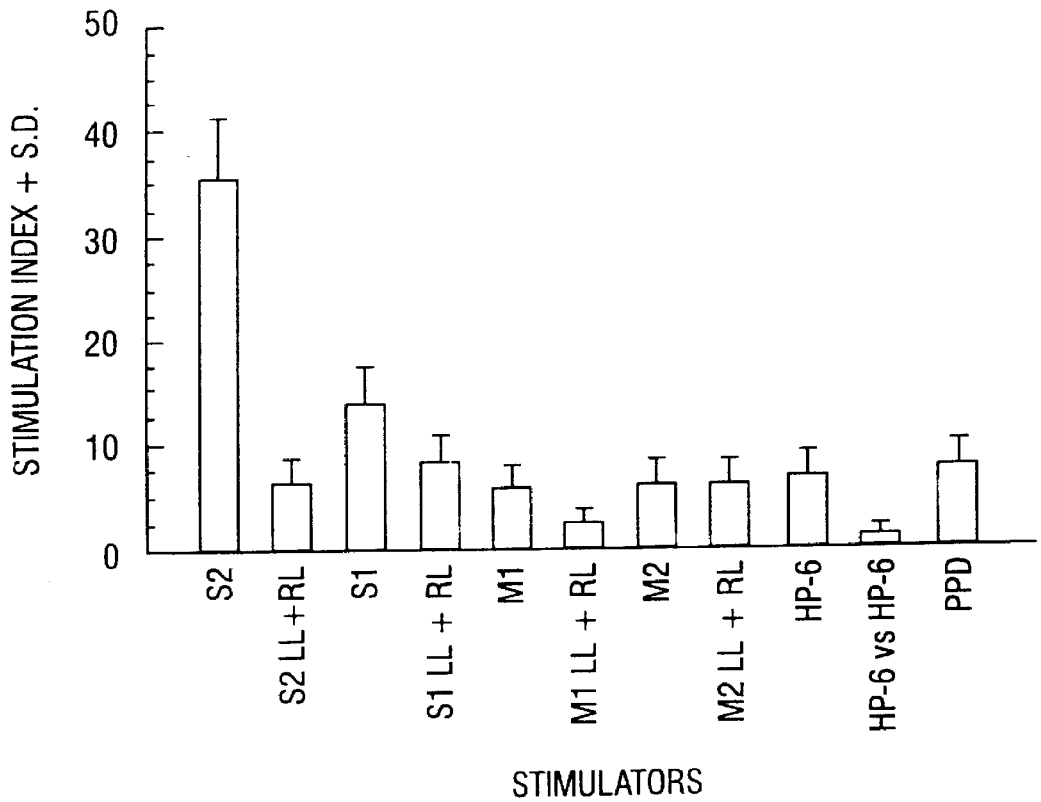
FIG. 7 shows the proliferative response of lymph node cells from S2 immunized ICR mice after exposure to the indicated stimulators.

The proliferative responses and standard deviations of cultured lymph node cells from ICR outbred mice immunized with S2 stock after stimulation with the indicated multimers and monomers are shown in FIG. 7. The S1 peptide was not immunogenic in these mice. The stimulation index (y axis) was obtained by dividing the radioactive counts of thymidine incorporated into stimulated cultures Thus the response in BALB/c mice was almost opposite of that observed for the ICR mice and shown in FIG. 7. The differences may be due to restriction and/or immunosuppression mediated by the S2 peptides in this strain of mice. Some specificity of the response to the HIV epitope is indicated from the difference of the response to itself and its linkers (17.9 vs 4.9). All the other responses were substantial and similar to the response mediated by PPD. These data indicate that the HIV epitope presented in the form of S1 multimers was not restricted and that the S1 peptide multimers broadly stimulated immune activities. This approach may bypass MHC restriction.

Table 4 shows the abilities of S20 and S22 to boost the proliferative response in lymph node cultures prepared from S2 immunized ICR nice. The increases were significant (P<0.001) and size related: S22>S20>Hp-6. Since all of the linker sequences are missing from HP-6 and most of them from S20 and S22, the data strongly suggest that the lymph node proliferative responses are specific for HP-6. Further, if the size of HP-6 is increased by adding two or four alternating hydrophobic and hydrophilic amino acid sequences, their ability to stimulate the lymph node cells is increased. In the same experiment, the S20 and S22 peptides inoculated into mice were not able to induce a proliferative response in mice. Thus, the linkers associated with HP-6 must be larger than two alternating hydrophobic or hydrophilic amino acid sequences in order to function as immunogens.

TABLE 4

Proliferation of Lymph Node Cell Cultures
Prepared from ICR Mice Immunized with S1 or S2 Peptides
and Stimulated with Truncated Forms of S2.

| Lymph Node Cultures Stimulated with: | (CPM × 6) ICR Mice Immunized with: | | | |
|---|---|---|---|---|
| | Tris-HCl | FCA | S1 + FCA | S2 + FCA |
| Media | 59.89 | 215.11 | 79.22 | 517.11* |
| S1 Stock | 73.67 | 114.33 | 126.33 | 240.56 |
| S2 Stock | 46.78 | 174.11 | 86.33 | 1884.22* |
| HP-6 | 97.11 | 179.78 | 84.22 | 1053.44* |
| S20 | 179.11 | 421.89 | 61.22 | 2492.22* |
| S22 | 172.11 | 466.11 | 97.56 | 3464.00* |
| PPD | 90.11 | 254.67 | 54.89 | 380.89 |
| SEA | 3383.78 | 3288.22 | 4984.56 | 3772.11 |

* = Significantly different from controls and each other (P < 0.001 by student's t test).

Table 4 also shows that the S1 peptide not only is non-immunogenic in ICR mice, but actually suppressed all the proliferative responses induced by culture stimulators with the exception of the S1 stock and SEA. Thus, depending on the allotype of the mouse (S1 is immunoenhancing in BALB/c mice, FIG. 19) multimeric peptides may be immunoenhancing or immunosuppressive. Application of immunosuppressive activities could be very important for suppression of autoimmune diseases, transplants, allergies, etc.

EXAMPLE 4

THE EFFECTS OF MULTIMERS ON LEUKOCYTE MORPHOLOGY

The present Example describes the different effects of multimers on leukocyte morphology.

Cultures prepared from Ficoll-hypaque enriched human leukocytes ($3\times10^6$/ml) were treated with the indicated M1, M2, S1, and S2 multimers (8 μg/ml) and observed under the microscope twice daily for five days. Photographs (100× normal or 200+ phase microscopy) were taken on days 1, 2, 3, 4, and 5. The parameters observed, compared, and photographed included: 1) cell clumping that was similar to clumping in the T cell mitogen staphylococcal enterotoxin A (SEA) treated cultures (0.2 μg/ml), and 2) large cell formation, either a) dendritic type, i.e., branched and/or elongated, or b) monocyte type, i.e., large oval. Observations and photographs showed that qualitative and quantitative types of morphological changes occurred depending on the multimers used to treat the cultures. The changes that occurred in the M1 treated cultures (8 μg/ml) by day 2 are representative of the overall changes. Similar changes occurred in the M2 treated cultures but were more pronounced than in the M1 treated cultures. These types of changes have occurred in six different human blood samples. In studies where the multimers were titrated in cultures, significantly different responses occurred down to<1.0 μg/ml. Thus, the multimers are potent.

A media control showed definitely less clumping than the others and the clumps were less dense. The clumping results were routinely observed in cultures treated with SEA. Treating cultures with the M2 stock that contained all the multimers resulted in the number of clumps being fewer than in the other treated cultures but more dense than those treated with the multimers eluted from the upper band (1) and next lower band (2). Cultures treated with band 1 contained numerous large clumps, while those treated with band 2 also contained larger clumps but were fewer in number. The clumps in both of these cultures were much larger than those observed in the SEA treated cultures. Numerous compact clumps were formed in cultures with bands 3 and 4. Band 3 caused larger clump formation while band 4 caused more numerous clumps to form. Induction or enhancement of cell adhesion factors, e.g., CD2, LFA-1, VLA, ICAM-1 etc., could be heavily involved in the observed clumping phenomena. When the cultures were tested for presence of IL-2 by ELISA, only the SEA stimulated cultures were positive; thus, the multimers are not mitogenic for naive T lymphocytes and cannot be considered as superantigens. Superantigens are known to induce apoptosis or toxicity and therefore would be considered as harmful components of a vaccine or other compounds to be used in vivo.

Cultures treated with the stock S1 and S2 monomers showed some minimal clumping. However, they did induce significant changes in the morphology of some cells. Both multimers caused the formation of numerous, large, round cells; and long, sometimes bulging cells, often with noticeable branching, while cultures treated with SEA lacked these morphologies. These cells resemble activated monocytes and dendritic cells, thus, they appear to be important in antigen presentation. Interestingly, cultures stimulated with stock S1 and S2 produced low levels of interferon gamma, an important immunomodulatory lymphokine. Since interleukin-2 (IL-2) was not detected in these cultures, the interferon gamma (IFN) was mQst likely not induced by IL-2; thus, its production resembles that of the early IFN gamma response that is thought to be important in up-regulating the immune response.

Together these findings show that there are significant differences in the biological activities of the stock multimers and the different sizes of multimers that can be isolated from them.

EXAMPLE 5

INDUCTION OF CYTOKINES IN NAIVE HUMAN BLOOD LEUKOCYTES

Because of the morphological changes observed in human leukocyte cultures treated with various multimers and the overall immunoactivity of multimers, their ability to induce cytokines associated with immunomodulation was investigated. The results are presented herein.

Briefly, enriched blood leukocyte cultures from one or two subjects were prepared as described in Example 4. Cultures were then incubated for four days in the presence of the indicated peptides and multimers (8 μg/ml) shown in FIG. 9 and FIG. 10. Following incubation, the supernatants were assayed for IL-1β, TNF-α, IFN-γ, and IL-10 by the ELISA method. IL-1β, TNF-α, and IFN-γ have been shown to be important up-regulators of immunoactivity and IL-10 is an important down-regulator.

Figure 9:
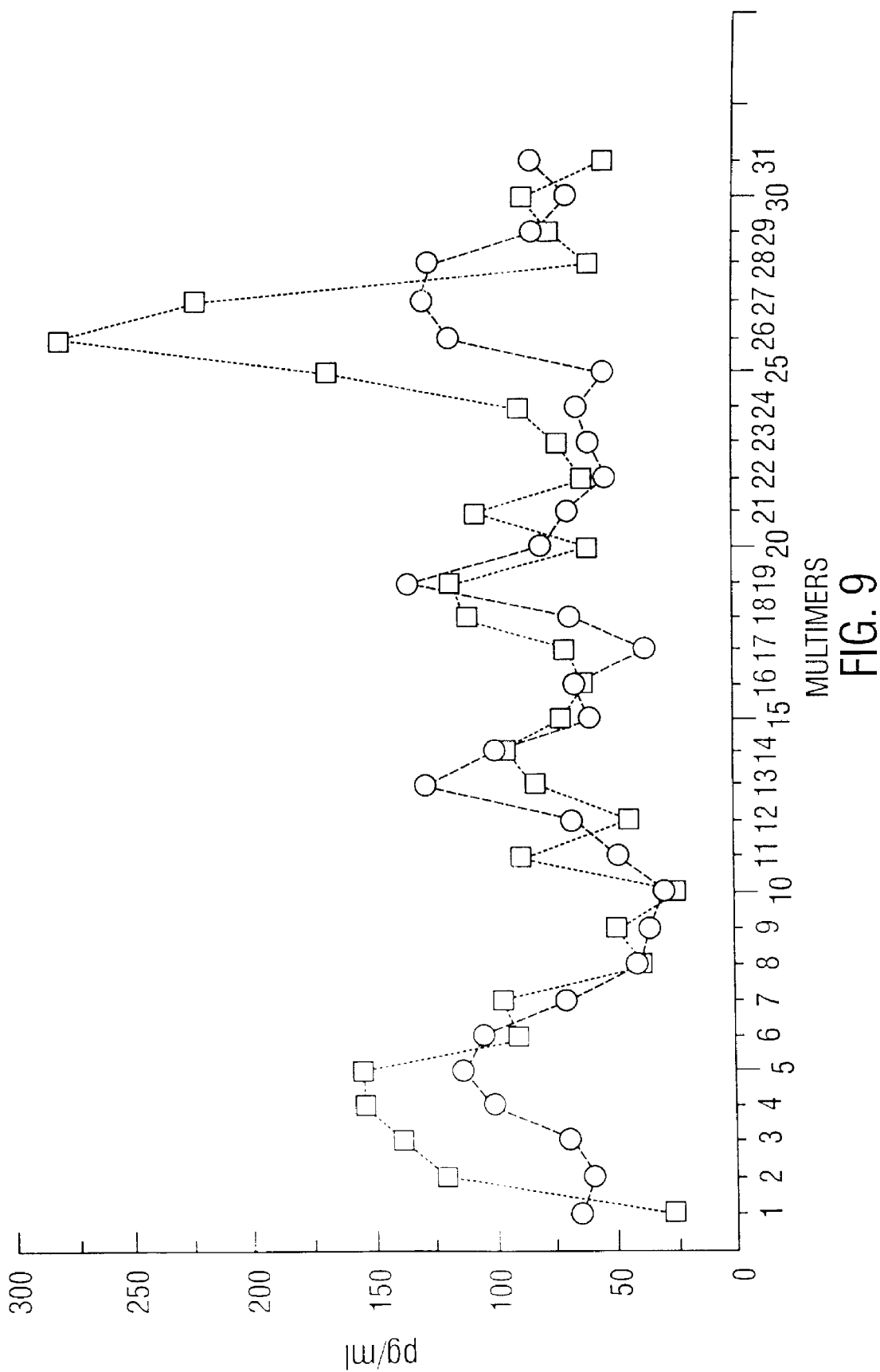
FIG. 9 shows IL-1B induction by treatment of naive human leukocytes with multimers. The legend is as follows: 1. Control; 2. M1 Stock; 3. M1 Band 1; 4. M1 Band 2; 5. M1 Band 3; 6. M1 Band 4; 7. M2 Stock; 8. M2 Band 1; 9. M2 Band 2; 10. M2 Band 3; 11. M1 Stock+M2 Stock; 12. M1 Band 1 +M2 Band 1; 13. M1 Band 2+M2 Band 2; 14. M1 Band 3+M2 Band 3; 15. M1 Left-linker; 16. M1 Right-linker; 17. M1 Left-linker+M1, Right-linker; 18. M2 Left-linker; 19. M2 Right-linker; 20. M2 Left-linker+M2, Right-linker; 21. M1 Left-linker+M2, Left-linker; 22. M1 Right-linker+M2, Right-linker; 23. M1 Left-linker+M2, Right-linker; 24. M1 Right-Linker+M2, Left-linker; 25. S1 Stock; 26. S2 Stock; 27. S1 Stock+S2 Stock; 28. S1 Left-linker+S2, Left-linker; 29. S1 Right-linker+S2, Right-linker; 30. S1 Left-linker +S2, Right-linker; 31. S1 Right-linker+S2, Left-linker.
Figure 10:
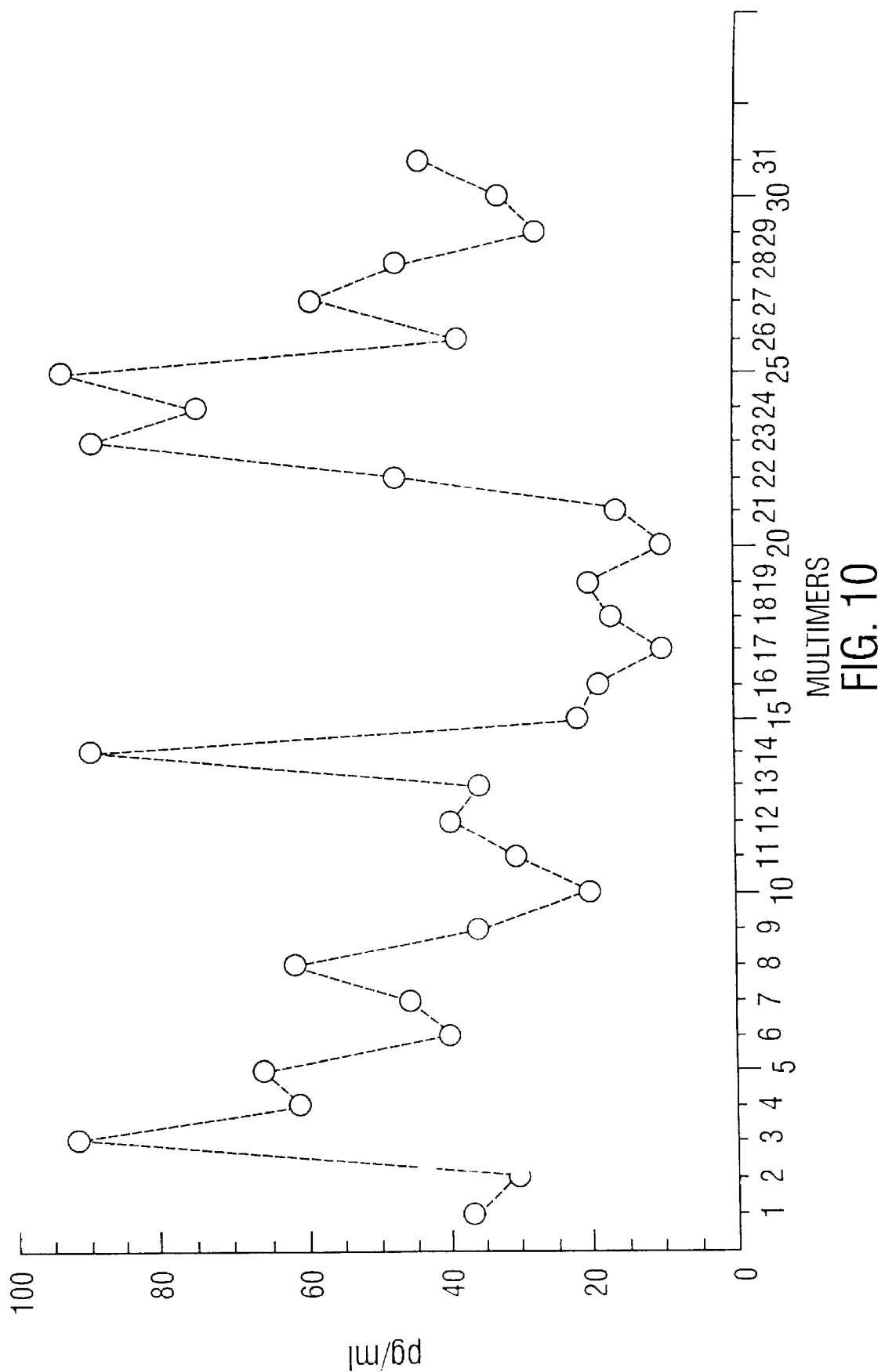
FIG. 10 shows IL-10 induction by treatment of naive human leukocytes with multimers. The multimer numbers are as in FIG. 9.

The results (FIG. 9, FIG. 10 and summary Table 5) indicate that the leukocytes from the two subjects reacted similarly for the production of Il-1β and TNF-α, i.e., many of the same peptides induced similar responses in both subjects when compared to the controls.

TABLE 5

Summary of Biological Activities of Multimers[a]

| | High | Medium | Low to +/− |
|---|---|---|---|
| Lymph node proliferative response in immunized mice. | | | |
| ICR mice | S2 stock M2 band 2 | S1 stock M2 band 1 | M2 stock |
| BALB/c mice | S1 stock | S2 stock | |
| Cytokine induction in naive human leukocytes. | | | |
| IFNγ | | | M2 stock and mixtures of M1 and M2 bands |
| IL-1β | S2 stock and S1 stock + S2 stock[b] | S1 stock M1 stock and top 3 M1 bands M2 RL | M1 band 4 and various linkers |
| TNF-α | S2 stock, M1 and 2 + M2 Band 2 M2 right linker M1 band 1 M1 band 2 | M1 band 1 + M2 band 1, M2 LL + M2 RL, S1 stock + S2 stock | M1 band 4 and various linkers M2 stock |
| IL-10 | M1 band 1 M1 band 3 + M2 band 3, M1 LL + M2 RL, M1 RL + M2 LL, S1 stock | M1 bands 2 and 3 M2 band 1 S1 stock + S2 stock | various M1, M2, S1 and S2 linker combinations |
| Morphological changes in naive leukocyte cultures: Cell clumping. | | | |
| Larger and fewer | M2 band 2 | M2 band 1 | M2 stock |
| Smaller and more numerous | M2 band 3 | M2 band 4 | |
| Macrophage and dendritic changes | S1 stock S2 stock S1 stock + S2 stock | | |

[a] — Relative activity of multimers compared to controls.
[b] — All combinations of peptides were used as mixtures.

Interestingly, some stock multimers and some, but not all, of the multimers isolated from gel bands isolated from those stocks were active. Thus there is specificity for the activity of the various multimers isolatable by PAGE performed on active stock preparations. Also, as expected, good inducers of IL-1β were also good inducers of TNF-α, since IL-1β induces synthesis of TNF-α. Overall, the studies indicate that stock preparations of multimers, multimeric species isolatable from stocks, or various combinations of these can be used to obtain various degrees of induction activity. This may be very important for optimizing responses at local systemic or oral sites of vaccine administration. In this regard, although this study was performed on human leukocytes, experiments in mice resulted in excellent lymph node proliferative responses (Table 1, FIG. 7 and FIG. 8). In addition, some of the linker sequences are active by themselves and thus may be valuable as adjuvants, e.g., the M2 right linker.

Figure 11:
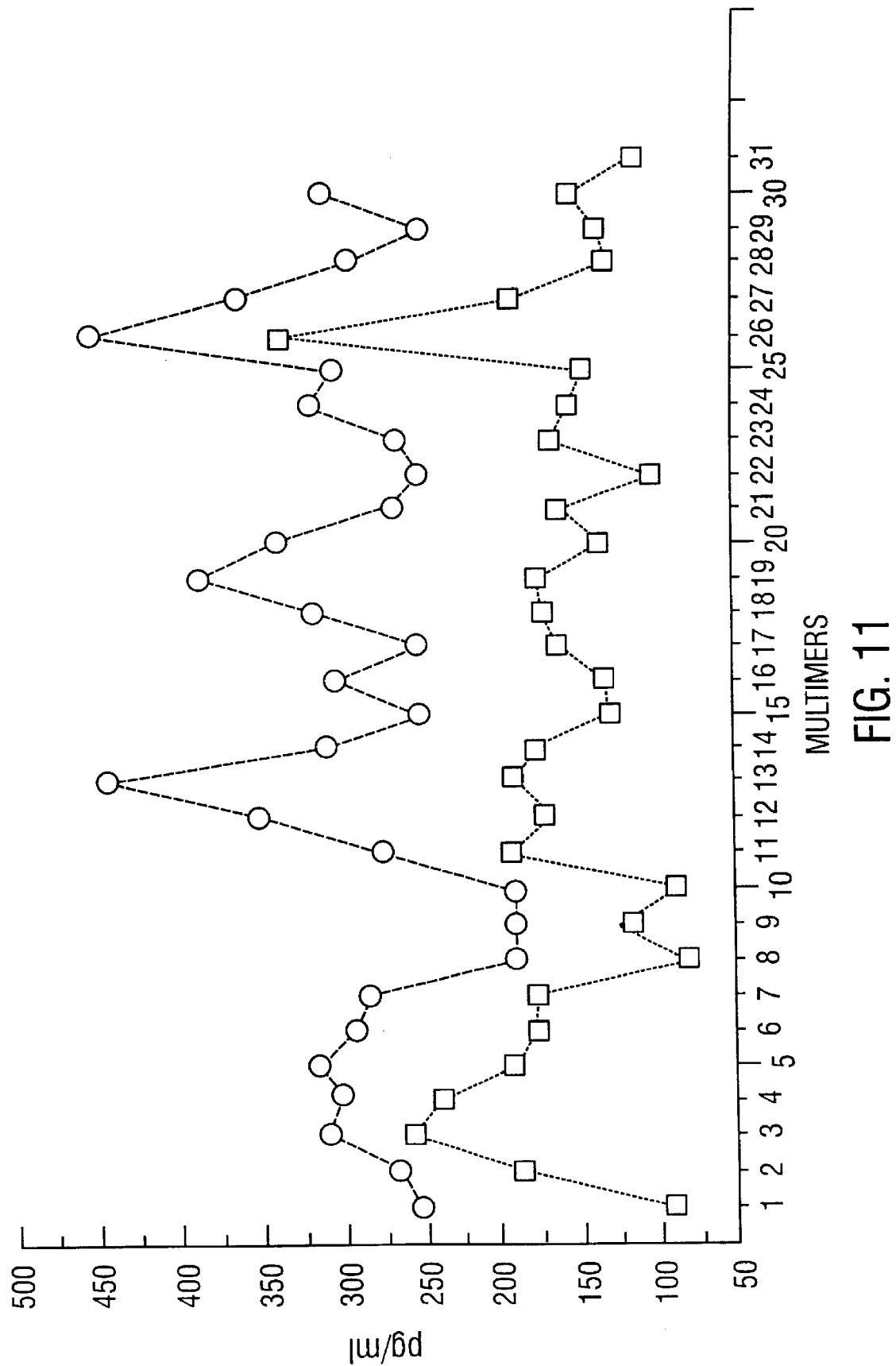

FIG. 11 shows a representative experiment of the IFN-γ response, as measured by ELISA. Inducers of IFN-γ, were mostly limited to the isolated M1 bands, M2 stock and mixtures of M1 and M2 bands. No IL-2 was detectable in the supernatants suggesting that the induction of IFN-γ was IL-2 independent and thus could be related to the early IFN-γ response that may be immunoenhancing. Since all the other multimers tested were negative, the data again indicate the specificity of certain multimers for a biological activity.

Figure 12:
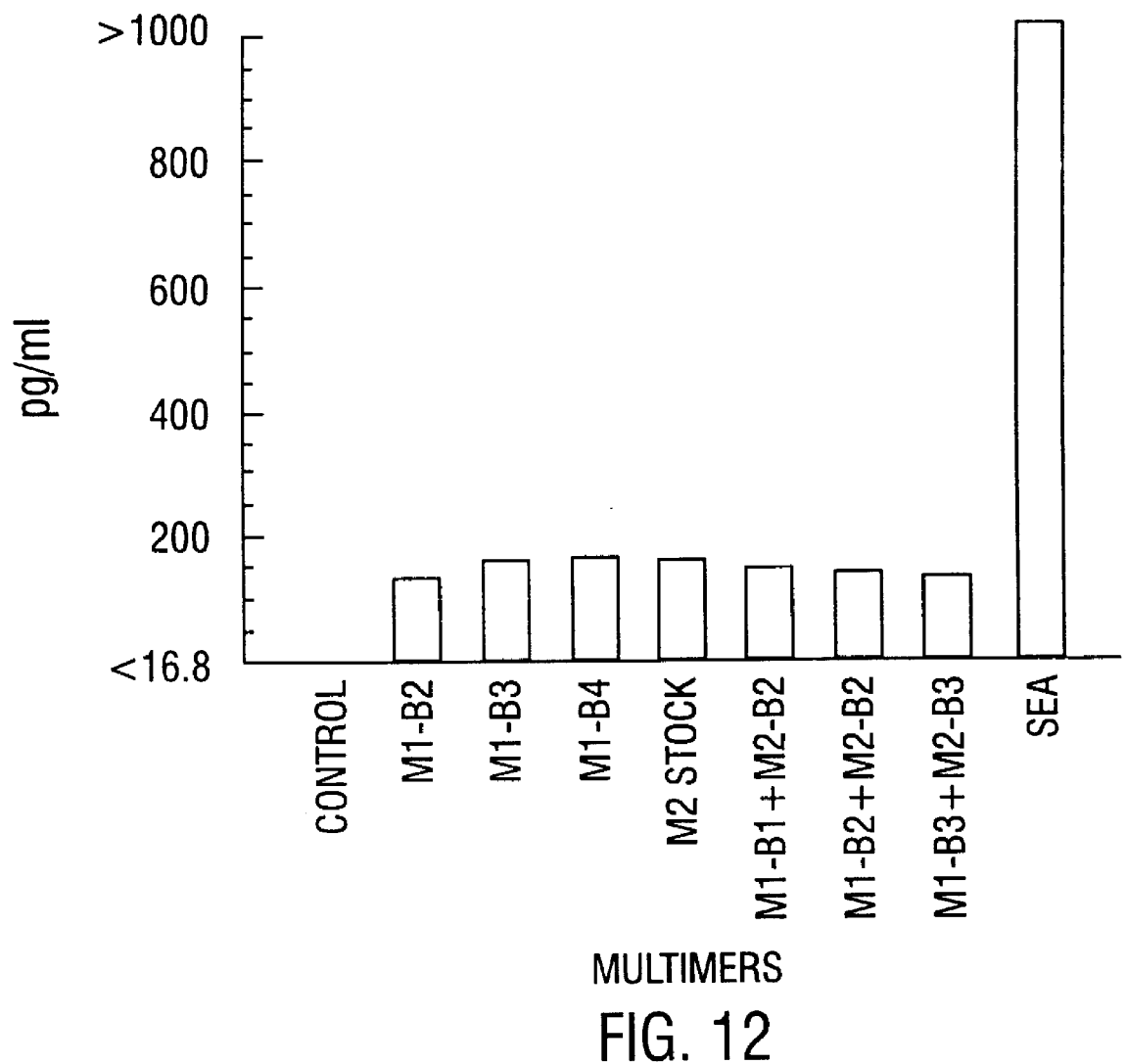
FIG. 12 shows interferon gamma induction by treatment of naive human leukocytes with peptide multimers.

FIG. 12 shows the IL10 response of naive human leukocytes treated with the various peptide multimers and stocks. The data indicate that the higher molecular weight multimers of M1 were better than the stock M1. Interestingly, the combination of lower sized M1 band 3 and M2 band 3 multimers was more active than any other combination. Thus, combinations of multimers may have activity that is different from the activities of the individual multimers that make them up. Combinations of the M1 and M2 linkers were also active and may be useful in suppressing immune responses. The S2 stock was also active and was also used to successfully immunize ICR but not BALB/c mice (FIG. 7 and FIG. 8). This ability to modulate human cytokines in leukocyte cultures provides a source of natural cytokines for use in humans or animals. The procedure here is the same as described in Example 7 below, except that human reagents are used.

EXAMPLE 6

USE OF MULTIMERS TO DETECT HIV ANTIBODIES IN SERA

Figure 13:
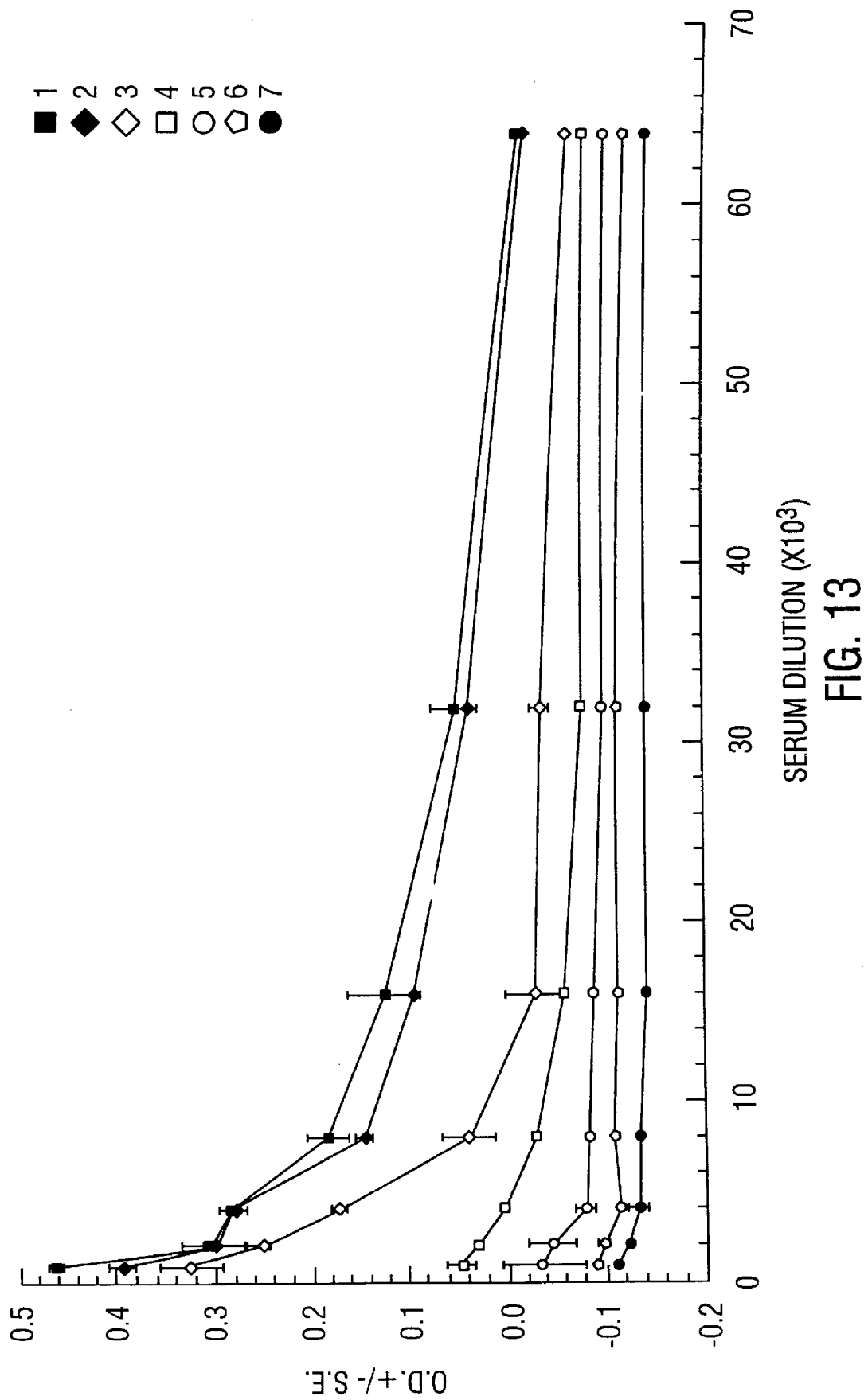
FIG. 13 shows binding of antibody in HIV positive serum to S2 peptide as determined in an EIA using the indicated quantity of peptide per well. The legend for FIG. 13 is: 3, 20 μg; 2, 10 μg; 1, 5 μg; 4, 1 μg, 5, 0.5 μg; 6, HP-6 (20 μg of HP-6); 7, normal serum (20 μg of S2).
Figure 14:
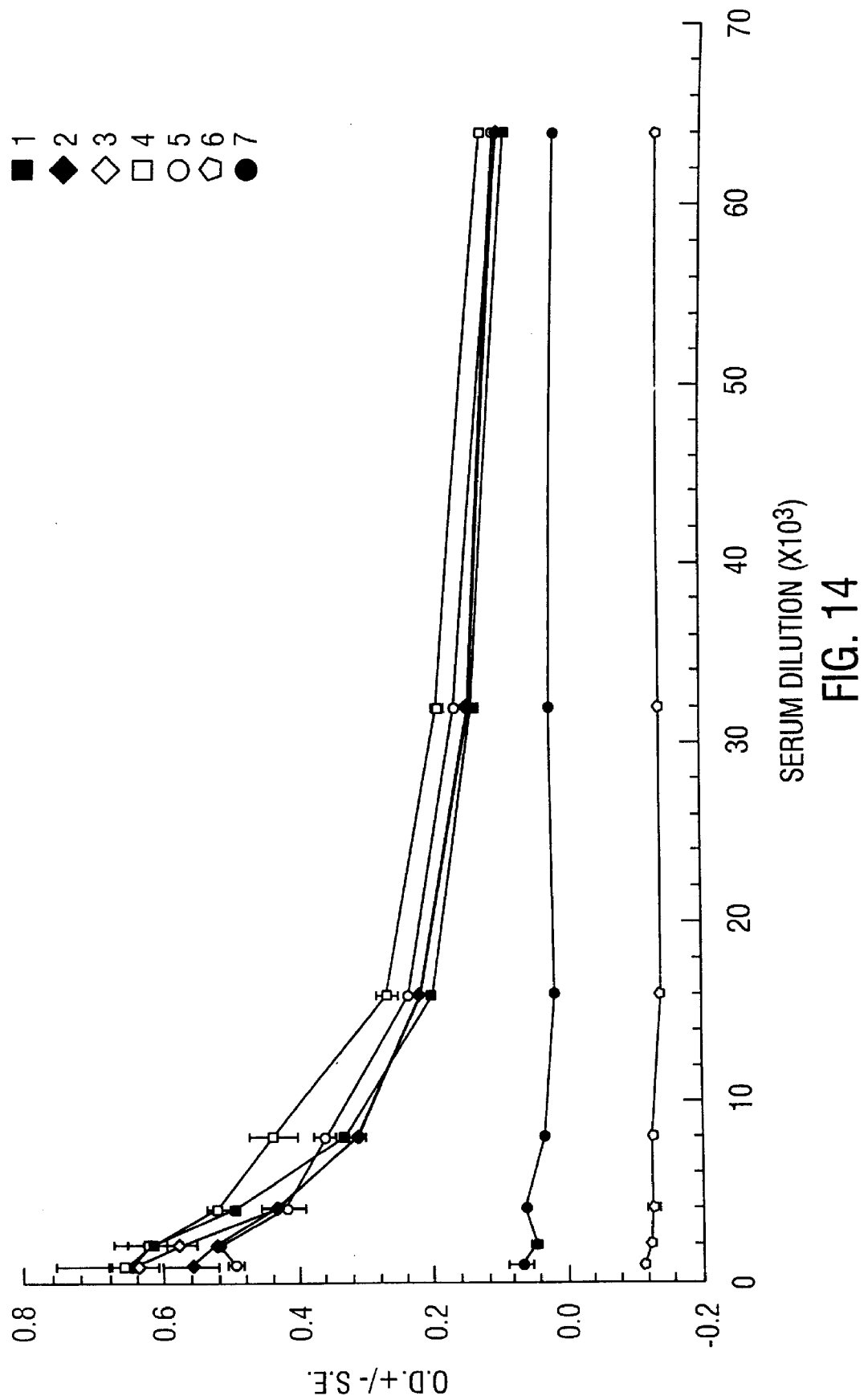
FIG. 14 shows binding of antibody in HIV positive serum to S1 peptide as determined in an EIA using the indicated quantity of peptide per well. The legend for FIG. 14 is: 3, 20 μg; 2, 10 μg; 1, 5 μg; 4, 1 μg, 5, 0.5 μg; 6, HP-6 (20 μg of HP-6); 7, normal serum (20 μg of S2).
Figure 15:
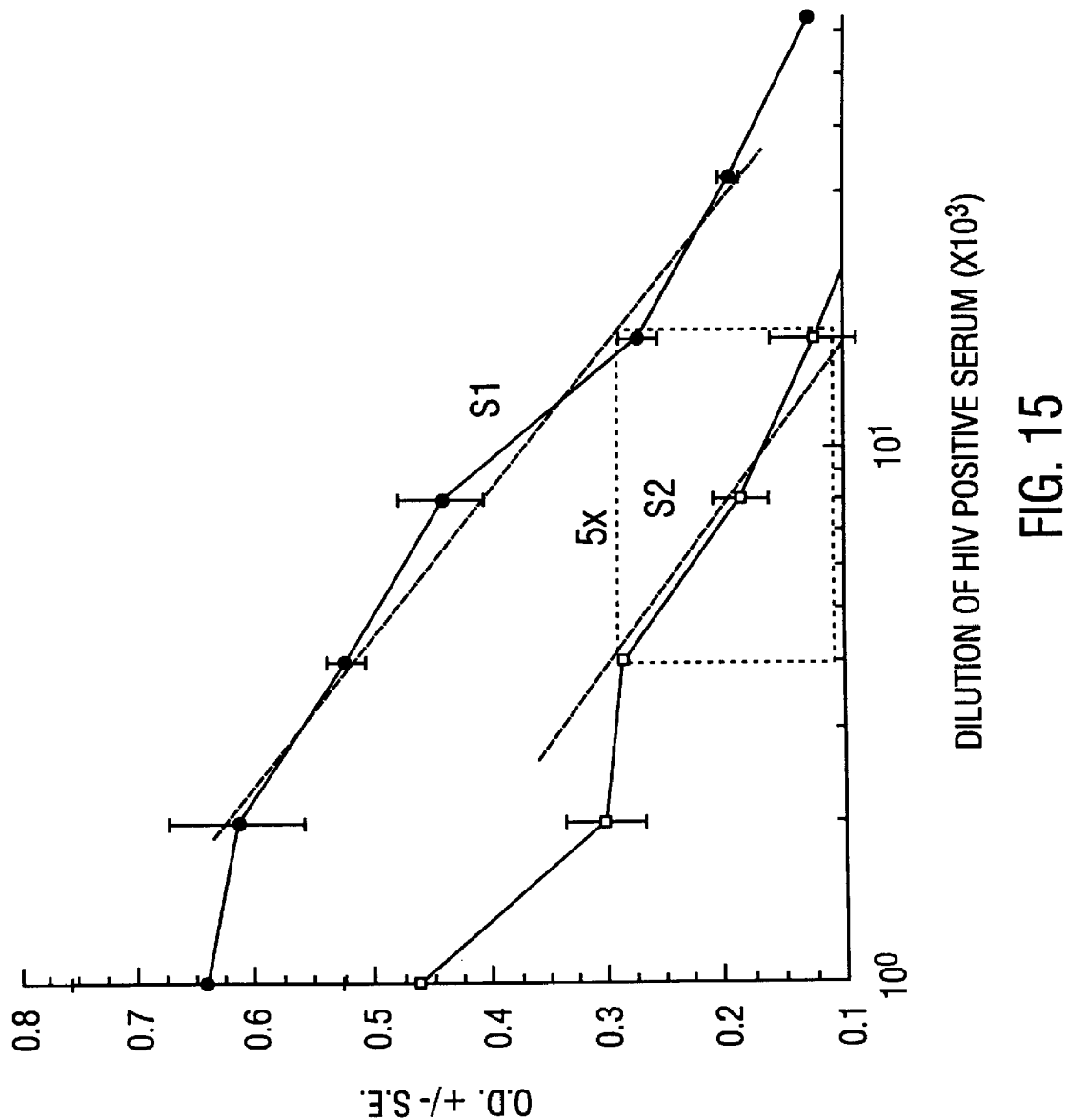
FIG. 15 shows binding activity of S1 vs. S2 for HP-6 antibody. The legend for FIG. 15 is: ●, 1 μg/well; □, 5 μg/well.

The present inventors have been able to assay antibody in known HIV positive sera in an ELISA, using the multimers containing the HIV epitope to bind the antibody (FIG. 13, 14 and 15). The titer was>1/64000/0.1 ml using an EIA assay with S1 peptide bound to wells. The bound S2 peptide was less efficient (FIG. 13 and 15) and depended on the amount of peptide bound to the wells. The epitope HP-6 alone did not bind antibody or normal serum IgG immunoglobulin. The ability to assay antibody to a single epitope has important implications for the specificity and usefulness of the anti-HIV antibody test.

The binding activity in the serum was measured by a routine sandwich method ELISA in which the indicated, 0.5 to 20 μg/well, of peptide dissolved in carbonate buffer was adsorbed overnight to microtiter wells. The following morning the wells were blocked with 0.1 percent bovine serum albumin. Then a 1:20 dilution of known positive patient serum or known negative control serum was added to each well for two hours followed by washing three times with PBS TWEEN-20. Affinity purified goat antibody to human IgG, conjugated to alkaline phosphatase (BIO-RAD) was then added followed by washing three times with PBS TWEEN-20. Phosphatase substrate was added and the color indicator allowed to develop for 30 minutes. The optical density (OD) was then read at 405 nm in a Molecular Devices Microplate Reader. The OD measurements resulting from binding of serum IgG to different quantities of peptide are shown in FIG. 13 and FIG. 14.

The present inventors envision the construction of a library of peptides for screening the responses of HIV patients for antibody and cellular responses to various antigens. Information gained in this way from survivors or long term survivors could be used to construct a vaccine that induced similar responses. In addition, it is known that the antigens in the multimers are being expressed in proper form for a vaccine and have much higher affinity for specific antibody than the antigen alone. This finding also strongly supports the data indicating the lymph node proliferative responses in mice were specific for the HIV epitope inter-linked in the multimers.

The fact that the binding is specific is indicated from the data in Table 6. This table shows the results of testing known positive (11 patients) and negative (15 subjects) serum samples from HIV positive and HIV negative patients. The data indicate that 10/11 positives were interpreted correctly, including #283–148 which was a +/− test in the Abbott EIA and 14/15 of the negative samples were interpreted correctly using an O.D. of 500 as the cut-off point.

Although the S2 peptide does not appear to be quite as efficient in binding antibody as the S1, the S2 peptides were used in these studies to strengthen the case that the lymph node proliferation abilities of S2 in ICR mice was specific for the HP-6 epitope and, often, the less sensitive test is the most specific. Also, ICR mice are outbred, as are humans. Data in FIG. 14 suggest that the HP-6 epitope in S1 is responsible for binding the antibody present in this known positive serum obtained from the NIH. Thus, the epitopes in the S1 and S2 peptides are present on the surface of the multimers in proper form. Therefore, ELISA assays could be developed using them that would be cheaper to produce than those presently used. Also, ELISA assays could be used to detect antibodies to various epitopes of the virus and mutant variations of the virus that would have important prognostic value and value for development of effective vaccines for many viruses. Also, ligands important in many biological activities could be presented in the multimers for activating or blocking purposes.

TABLE 6

Results of ELISA Test for Antibody in HIV Positive or Negative Serum Using S2 Peptide (5 μg or 1 μg/well)

| Patient and Serum Sample No. | Absorbance | Result of Present Invention | Known Result[a] |
|---|---|---|---|
| | | 5 μg/well | |
| 5 | 0.071 | – | – |
| 3 | 0.101 | – | – |
| 8 | 0.164 | – | – |
| 9 | 0.169 | – | – |
| 4 | 0.178 | – | – |
| 1 | 0.186 | – | – |
| 10 | 0.218 | – | – |
| 300-1598 | 0.243 | –[b] | + |
| 2 | 0.272 | – | – |
| 300-1665 | 0.304 | – | – |
| 6 | 0.336 | – | – |
| 307-1850 | 0.412 | – | – |
| 7 | 0.445 | – | – |
| 299-2151 | 0.446 | – | – |
| 8025 | 0.501 | +/– | – |
| 300-1856 | 0.530 | + | + |
| 300-1593 | 0.539 | + | + |
| 283-1448 | 0.588 | + | +/–[c] |
| 306-1669 | 0.670 | + | + |
| 307-1758 | 0.708 | + | + |
| 306-2872 | 1.061 | + | + |
| 300-1773 | 1.265 | + | + |
| | | 1 μg/well | |
| 264-1699 | 0.169 | – | – |
| 300-1861 | 0.363 | + | + |
| 306-2046 | 0.386 | + | + |
| 304-2945 | 0.506 | + | + |
| NIH[d] | 0.760 | + | + |

[a] — Abbott Laboratories EIA
[b] — Possible no antibody to HP-6 epitope
[c] — Positive by fluorescence test
[d] — Known positive serum from National Institute of Health Since the M peptides do not bind antibody in HIV positive serum, it appears that the antigens are not accurately portrayed on the surface of the multimers. However, the data of Table 1 demonstrate that, if mice are immunized with the M2 band 2 multimer, a specific lymph node proliferative response to HP-6 is elicited. Thus, it would appear that the antigens become accurately presented on the surface of antigen presenting cells after intracellular processing of the non-covalently bound multimers. Unlinked peptides are normally presented directly on the surface of the cell and for this reason are often less immunogenic. This type of presentation of peptide antigen is useful for intracellular modulation of the immune response. Practically, this means that antigens that are not presented properly by a defective immune system may, in fact, be sandwiched with linkers and presented properly. In addition, although the M1 and M2 monomers did not bind HIV antibody (probably because the peptides are not situated in the proper position on the multimers), they and their linkers' abilities to induce IL-1β, TNF-α, IFN-gamma, and IL-10 are still important, as well as their ability to immunize mice to the extent that their lymph node cells respond to stimulation by the HIV epitope, HP-6 (Table 1). Again, this latter fact probably results from the way the non-covalently bound multimers are processed by antigen presenting cells.

EXAMPLE 7

INDUCTION OF ANTIBODIES TO HIV EPITOPE HP-6 FOLLOWING IMMUNIZATION WITH MULTIMERIC PEPTIDES

ELISA Assay for Antibody:

The antibody in the serum was measured by a routine sandwich method ELISA assay in which 2.0 μg/well of peptide dissolved in carbonate buffer was adsorbed overnight to microtiter wells. The following morning the wells were blocked with 0.1 percent bovine serum albumin. Then a 1:20 dilution of serum was added to each well for two hours followed by washing three times with PBS Tween-20. Polyclonal antibody to mouse IgM, IgG and IgA, or affinity purified antibody to IgG, conjugated to alkaline phosphatase (BIO-RAD) was then added followed by washing three times with PBS Tween-20. Phosphatase substrate was added and the color indicator allowed to develop for 30 minutes. The optical density (OD) was then read at 405 nm in a Molecular Devices Microplate Reader. The OD measurements are shown in Tables 7, 8, 9 and 10. The results, OD readings at least four fold greater than controls and OD readings greater than 0.125 and statistical significance, when possible to determine, are underlined readings with asterisks.

Results:

Groups of ICR mice, three (A, B, C)/group, were injected subcutaneously at the base of the tail with the indicated multimeric peptides emulsified in Freund's complete (FCA) or incomplete adjuvant (FIA). Blood was collected and pooled at three weeks post-immunization and tested (see ELISA assay above) singly to screen for early development of IgM, IgA and/or IgG antibody to multimers (Table 7).

TABLE 7

Levels of Antibodies to Multimers and HIV Epitope HP-6 in Individual ICR Mice 3 and 5 Weeks after Immunization

| ANTISERUM/ | FCA | | | | | IFA | | | | |
|---|---|---|---|---|---|---|---|---|---|---|
| | 3 WKS | | | | 5 WKS | 3 WKS | | | | 5 WKS |
| ANTIGEN | CTRL | POOLED | A | B | C | CTRL | POOLED | A | B | C |
| M1/M1 | .071 | .173 | .098 | .133 | .173 | .029 | .094 | .092 | .070 | .077 |
| M2/M2 | .013 | .049 | .124 | .021 | .030 | .000 | .080 | .032 | .051 | .021 |
| S1/S1 | .065 | .482 | .525 | .081 | .204 | .033 | .223 | .509 | .244 | .026 |
| S2/S2 | .100 | .112 | .118 | .091 | .081 | .040 | .070 | .062 | .058 | .088 |
| M2.B1/M2.B1 | — | .018 | — | .002 | .003 | .025 | .029 | .029 | .035 | .066 |
| M2.B2/M2.B2 | .004 | .047 | .020 | .012 | .034 | .025 | .044 | .044 | .028 | .035 |
| M2.B3/M2.B3 | .002 | — | .018 | .007 | .012 | .010 | .027 | .014 | .016 | .020 |
| M2.B1/M2 | .002 | .038 | .006 | .027 | .036 | −.010 | .064 | .000 | .001 | .066 |
| M2.B2/M2 | .009 | .078 | .040 | .019 | .028 | .001 | .073 | .011 | .003 | .037 |
| M2.B3/M2 | .005 | — | .032 | .013 | .011 | .000 | .021 | .000 | .000 | .012 |
| FCA/FCA | .001 | .006 | .002 | .001 | −.010 | | | | | |
| IFA/IFA | | | | | | .002 | .000 | −.001 | .003 | .010 |
| M1/HP.6 | .010 | .234 | .086 | .147 | .222 | .010 | .131 | .103 | .035 | .036 |
| M2/HP.6 | .005 | .162 | 192 | .116 | .074 | — | .117 | .015 | .046 | .030 |
| S1/HP.6 | .014 | .333 | .151 | .027 | .257 | .003 | .156 | .055 | .225 | .005 |
| S2/HP.6 | .008 | .085 | .201 | .110 | .038 | .005 | .115 | .085 | .071 | .124 |
| M1/S2.20 | .009 | .163 | .062 | .109 | .172 | .008 | .026 | .009 | .010 | .016 |
| M2/S2.20 | .003 | .114 | .139 | .073 | .061 | .001 | .025 | .002 | .013 | .009 |
| S1/S2.20 | .008 | .242 | .092 | .020 | .161 | .007 | .024 | .006 | .023 | .002 |
| S2/S2.20 | .018 | .071 | .094 | .073 | .025 | .004 | .024 | .023 | .022 | .048 |
| M1/S2.22 | .004 | .061 | .042 | .056 | .065 | .005 | .010 | .017 | .021 | .027 |
| M2/S2.22 | .005 | .061 | .075 | .044 | .038 | .003 | .016 | .003 | .017 | .010 |
| S1/S2.22 | .010 | .152 | .181 | .020 | .185 | .001 | .017 | .005 | .025 | — |
| S2/S2.22 | .003 | .036 | .058 | .057 | .030 | — | .012 | .023 | .031 | .048 |
| M2.B1/HP.6 | .014 | .137 | .020 | .020 | .030 | .005 | .093 | .009 | .001 | .027 |
| M2.B2/HP.6 | .020 | .165 | .090 | .141 | .071 | .003 | .141 | .017 | .012 | .064 |
| M2.B3/HP.6 | .013 | .008 | .097 | .045 | .015 | .007 | .025 | .006 | .007 | .009 |
| FCA/HP.6 | 0.19 | — | .032 | .081 | .004 | | | | | |
| IFA/HP.6 | | | | | | .016 | .034 | .023 | .028 | |
| M2.B1/S2.20 | .007 | .099 | .027 | .021 | .038 | .066 | .025 | .006 | .003 | .016 |
| M2.B2/S2.20 | .009 | .145 | .070 | .086 | .041 | .008 | .029 | .019 | .005 | .011 |
| M2.B3/S2.20 | .009 | .000 | .069 | .025 | .000 | .006 | .013 | .004 | .005 | .004 |
| FCA/S2.20 | .010 | — | .020 | .039 | .000 | | | | | |
| IFA/S2 .20 | | | | | | .014 | .016 | .014 | .006 | |
| M2.B1/S2.22 | .004 | .062 | .011 | .024 | .039 | .010 | .007 | .000 | .001 | .013 |
| M2.B2/S2.22 | .011 | .103 | .055 | .057 | .074 | .000 | .020 | .016 | .002 | .009 |
| M2.B3/S2.22 | .018 | .016 | .039 | .020 | .007 | .001 | .005 | .000 | .001 | .001 |
| FCA/S2.22 | .008 | — | .027 | .035 | .002 | | | | | |
| IFA/S2.22 | | | | | | .006 | .009 | .011 | .001 | |

Serum collected at five weeks post immunization from individual mice was also tested singly for screening purposes (Table 7). Table 8 shows the results and significance (Student's t test) of selected individual serum samples from the mice in Table 7 when measured in duplicate for statistical purposes and when sufficient sample was available.

TABLE 8

Levels of Antibodies to Multimers in Individual ICR Mice 3 and 5 Weeks After Immunization

| Antiserum/ | FCA | | | | | FIA | | | | |
|---|---|---|---|---|---|---|---|---|---|---|
| | 3 WEEKS | | 5 WKS | | | 3 WEEKS | | 5 WKS | | |
| Antigen | CONTROL | POOLED | A | B | C | CONTROL | POOLED | A | B | C |
| S/M1 | 0.007 | 0.218** | 0.100 | 0.008 | 0.076 | 0.002 | 0.269*** | | 0.130* | 0.068 |
| S2/M1 | <0.0 | | 0.035 | 0.037 | 0.042 | | 0.502** | | | 0.044 |
| M1/M1 | 0 | 0.512** | 0.687** | 0.353** | 0.107* | 0.00 | | 0.443* | 0.353* | 0.457* |
| M2/M1 | 0.010 | | 0.028 | 0.043 | 0.194 | | | | | |
| M2.B2/M1 | <0.0 | 0.100* | 0.066 | 0.043 | 0.021 | | | | | |
| M2.B3/M1 | 05 | | 0.004 | | 0.036 | | | | | |
| | 0.0 | | | | | | | | | |
| | 0.003 | | | | | | | | | |
| S1/M2 | 0.007 | 0.218** | 0.120 | 0.023 | 0.038 | 0.00 | 0.097 | | 0.097 | 0.025 |
| S2/M2 | 0.00 | | 0.026 | 0.017 | 0.041 | 0.066 | | | | |
| M1/M2 | 0.011 | 0.137* | 0.084 | 0.059 | 0.038 | 0.005 | 0.071 | 0.064 | 0.010 | 0.009 |
| M2/M2 | 0.00 | | 0.015 | 0.026 | 0.181* | | | | | |

TABLE 8-continued

Levels of Antibodies to Multimers in Individual ICR Mice 3 and 5 Weeks After Immunization

| Antiserum/ | FCA | | | | | FIA | | | | |
|---|---|---|---|---|---|---|---|---|---|---|
| | 3 WEEKS | 5 WKS | | | | 3 WEEKS | 5 WKS | | | |
| Antigen | CONTROL | POOLED | A | B | C | CONTROL | POOLED | A | B | C |
| M2.B2/M2 | 0.003 | 0.069 | 0.050 | 0.022 | 0.009 | | | | | |
| M2.B3/M2 | 0.000 | | 0.003 | | 0.029 | | | | | |
| S1/S1 | <0.0 | 0.663** | 0.090 | <0.0 | | 0.033 | 0.282** | | 0.084 | 0.839** |
| S2/S1 | 0.012 | 0.005 | <0.0 | 0.041 | 0.890** | | | | | |
| M1/S1 | <0.0 | 0.097 | 0.075 | 0.293** | <0.0 | 0.006 | 0.525* | 0.285** | 0.144 | 0.092 |
| M2/S1 | 0.014 | | <0.0 | <0.0 | <0.0 | | | | | |
| M2.B2/S1 | <0.0 | 0.035 | 0.047 | 0.037 | 0.039 | | | | | |
| M2.B3/S1 | <0.0 | 0.069 | <0.0 | | 0.025 | | | | | |
| | | | | | <0.0 | | | | | |
| S1/S2 | 0.022 | 0.197** | 0.134* | 0.029 | 0.096 | <0.0 | 0.171** | | 0.103** | 0.318** |
| S2/S2 | 0.001 | 0.047 | 0.037 | | 0.035 | | | | | |
| M1/S2 | 0.057 | 0.334* | 0.407* | | 0.040 | 0.008 | 0.446* | 0.202** | 0.114** | 0.045 |
| M2/S2 | 0.018 | | 0.046 | 0.406*** | 0.216** | | | | | |
| M2.B2S21 | 0.012 | 0.112** | 0.072 | 0.208* | 0.004 | | | | | |
| M2.B3/S2 | 0.029 | | 0.070 | 0.035 | 0.055 | | | | | |
| | | | | | 0.055 | | | | | |

*P ≤ 0.005
*P ≤ 0.005
***P = 0.1 to 0.049

Table 9 shows the results and significance of duplicate measurements of the antibody response to multimers and linkers five weeks after the second immunization with the indicated multimers.

TABLE 9

Levels of Antibodies to Multimers and HIV Epitope HP-6 Linkers and in Individual ICR Mice 5 Weeks After Second Immunization

| Antiserum/ | FCA | | | FIA | | |
|---|---|---|---|---|---|---|
| Antigen | A | B | C | A | B | C |
| S1/M1 | 0.075 | 0.133*** | 0.303** | 0.166* | 0.077 | |
| S2/M1 | 0.047 | 0.114 | 0.067 | 0.062 | 0.090 | 0.108** |
| M1/M1 | 0.307* | 0.074 | 0.354* | 0.250*** | 0.323*** | 0.335*** |
| M2/M1 | 0.257** | 0.022 | 0.083 | 0.128** | 0.243* | — |
| M2.B1/M1 | 0.053 | 0.037 | 0.013 | 0.086 | — | 0.168** |
| M2.B2/M1 | 0.108 | 0.098 | 0.269* | 0.061 | 0.023 | 0.014 |
| M2.B3/M1 | 0.060 | 0.02 | 0.072 | 0.001 | 0.012 | 0.021 |
| FCA/M1 | 0.085 | 0.078 | — | 0.067 | 0.047 | — |
| S1/M2 | 0.034 | 0.078 | 0.217** | 0.085 | 0.047 | — |
| S2/M2 | 0.022 | 0.051 | 0.042 | 0.057 | 0.067 | 0.110** |
| M1/M2 | 0.081 | 0.084 | 0.087 | 0.034 | 0.043 | 0.117** |
| M2/M2 | 0.148* | 0.017 | 0.047 | 0.076 | 0.167* | — |
| M2.B1/M2 | 0.020 | 0.025 | 0.026 | 0.103* | 0.003 | 0.076 |
| M2.B2/M2 | 0.069 | 0.066 | 0.100 | 0.022 | 0.023 | 0.021 |
| M2.B3/M2 | 0.038 | 0.005 | 0.012 | 0.008 | 0.014 | 0.024 |
| FCA/M2 | 0.072 | 0.059 | — | 0.057 | 0.028 | — |
| S1/S1 | 0.231** | 0.390*** | 0.752** | 0.648** | 0.664* | — |
| S2/S1 | 0.017 | 0.058 | 0.012 | 0.047 | 0.095 | 0.080 |
| M1S1 | 0.255** | 0.075 | 0.089 | 0.034 | 0.223** | 0.200* |
| M2/S1 | 0.108* | 0.024 | 0.016 | 0.075 | 0.153** | — |
| M2.B1/S1 | 0.035 | 0.022 | 0.023 | 0.041 | 0.003 | 0.094 |
| M2.B2/S1 | 0.089 | 0.046 | 0.126* | 0.015 | 0.031 | 0.026 |
| M2B3/S1 | 0.053 | 0.008 | 0.109 | 0.003 | 0.012 | 0.0 |
| FCA/S1 | 0.039 | 0.049 | — | 0.053 | 0.029 | — |
| S1/S2 | 0.053 | 0.067 | 0.140** | 0.063 | 0.159* | — |
| S2/S2 | 0.040 | 0.084 | 0.076 | 0.027 | 0.069 | 0.054 |
| M1/S2 | 0.082 | 0.044 | 0.105* | 0.036 | 0.066 | 0.201* |
| M2/S2 | 0.214** | 0.019 | 0.010 | 0.107* | 0.224* | — |
| M2/B1/S2 | 0.045 | 0.027 | 0.057 | 0.076 | 0.003 | 0.069 |
| M2.B2/S2 | 0.164* | 0.119 | 0.177*** | 0.013 | 0.015 | 0.016 |
| M2.B3/S2 | 0.050 | 0.036 | 0.065 | 0.019 | 0.012 | 0.041 |
| FCA/S2 | 0.024 | 0.116 | | 0.055 | 0.075 | — |
| M1/HP.6 | 0.083 | 0.131 | 0.162* | 0.028 | 0.042 | 0.070 |

TABLE 9-continued

Levels of Antibodies to Multimers and HIV Epitope HP-6 Linkers and in Individual ICR Mice 5 Weeks After Second Immunization

| Antiserum/ | FCA | | | FIA | | |
|---|---|---|---|---|---|---|
| Antigen | A | B | C | A | B | C |
| M2/HP.6 | 0.126* | 0.034 | 0.121* | 0.118*** | 0.127* | — |
| S1/HP.6 | 0.033 | 0.105*** | 0.388** | 0.194** | 0.033 | — |
| S2/HP.6 | 0.044 | 0.084 | 0.060 | 0.064* | 0.120** | 0.147** |
| M2.B1/HP.6 | 0.019 | 0.044 | 0.010 | 0.006 | 0.004 | 0.056 |
| M2.B2/HP.6 | 0.088 | 0.097* | 0.110* | 0.024 | 0.032 | 0.029 |
| M2.B3/HP.6 | 0.028 | 0.013 | 0.025 | 0.017 | 0.001 | 0.023 |
| FCA/HP.6 | 0.051 | 0.051 | 0.051 | | | |
| FIA/HP.6 | | | | 0.035 | 0.035 | 0.035 |
| S1.S1.LL | | 0.013 | 0.014 | 0.117** | 0.035 | 0.011 | — |
| S2.S1.LL | 0.008 | 0.013 | 0.018 | 0.030 | 0.069 | 0.050 |
| S1/S2.LL | 0.016 | 0.020 | 0.140** | 0.035 | 0.010 | — |
| S2/S2.LL | 0.012 | 0.014 | 0.013 | 0.024 | 0.044 | 0.045 |
| FCA/S1.LL | 0.017 | 0.034 | — | 0.025 | 0.008 | — |
| FIA/S1.LL | | | | | | |
| S1/S1.RL | 0.021 | 0.075 | 0.198* | 0.071 | 0.020 | — |
| S2/S1.RL | 0.006 | 0.018 | 0.026 | 0.040 | 0.069 | 0.065 |
| S1/S2.RL | 0.004 | 0.011 | 0.155** | 0.022 | 0.003 | — |
| S2/S2.4L | 0.005 | 0.007 | 0.005 | 0.018 | 0.034 | 0.057 |
| FCA/S1.RL | 0.050 | 0.025 | — | | | — |
| FIA/S1.RL | | | | 0.031 | 0.009 | |
| FCA/S2.RL | 0.011 | 0.020 | — | | | — |
| FIA/S2.RL | | | | 0.025 | 0.005 | |

*P ≦ 0.05
**P ≦ 0.005
***P = 0.1 to 0.049

Table 10 shows the results and significance of the IgG response of individual mice to the multimers five weeks after the second immunization, when sufficient sample was available.

TABLE 10

Levels of IgG antibody to peptides of individual ICR mice 5 weeks after second

| Antiserum/Peptide | FCA | | | FIA | | |
|---|---|---|---|---|---|---|
| Antigen | A | B | C | A | B | C |
| S1/S1 | 1.190** | 2.163*** | 2.148*** | 2.30*** | 2.325*** | — |
| S2/S1 | 0.060 | 0.140*** | 0.124*** | 0.170*** | 0.537*** | 0.202** |
| FCA/S1 | 0.1775 | 0.133 | — | | | |
| FIA/S1 | | | | 0.176 | 0.098 | — |
| Control/S1 | 0.013 | | | 0.013 | | |
| S1/S2 | 0.123 | 0.390* | 1.00*** | 0.525*** | 0.768*** | — |
| S2/S2 | 0.82 | 0.163* | 0.132 | 0.091 | 0.321** | 0.134 |
| FCA/S2 | 0.093 | 0.099 | | | | |
| FIA/S2 | | | | 0.170 | 0.116 | |
| Control/S2 | 0.014 | | | 0.014 | | |
| M1/M1 | 1.518*** | 0.115 | 1.637*** | 1.476*** | 1.576*** | 1.592*** |
| M2/M1 | 0.832*** | 0.045 | 0.124*** | 0.583*** | 1.049*** | — |
| FCA or FIA/M1 | 0.060 | 0.034 | | 0.071 | 0.028 | |
| Control/M1 | 0.007 | | | 0.007 | | |
| M1/M2 | 0.068 | 0.01 | 0.124 | 0.009 | 0.020 | 0.189* |
| M2/M2 | 0.393* | 0.021 | 0.02 | 0.102 | 0.389 | |
| FCA or FIA/MS | 0.040 | 0.015 | — | 0.046 | 0.007 | — |
| Control/M2 | 0.002 | | | 0.002 | | |

*P ≦ 0.05
**P ≦ 0.01
***P ≦ 0.001
doubly underlined values indicate where crossreactivity occurred.

The data in Tables 7 and 8 show that antibodies to multimeric peptides S1 and M1 were induced against S1 and M1, respectively, in two out of three mice in the presence of FCA or FIA. More importantly all the stock peptides induced antibody to the HIV HP-6 peptide in one to two mice per group of three, indicating that the multimer could induce specific antibody to the HIV epitope sandwiched between the linkers. Multimers S1 and M1 worked most effectively in this study. Antibodies to S1 also reacted with the truncated S20 and S22 peptides, further indicating specificity. Antibodies to M1 also reacted with HP-6, but to a lesser extent. Antibodies to HP-6 were also induced by M2 band 2, the same multimer that induced a significant proliferative response in these mice (Table 1). Thus, this result supports the specificity of the proliferative response for HP-6.

Table 9 shows the potential IgM, IgA and IgG antibody responses to the multimers, HP-6 and linkers five weeks after the second immunization. It was observed that all the mice tested produced significant amounts of antibody to the S1 and S2 peptides. S1 also induced antibodies in some of the mice immunized with M1, S2 or M2 peptides. The only common modality in these peptides with the S1 peptide is the HP-6 epitope, thus the data suggests that the antibodies detected reacted to the HP-6 epitope. This is supported by the fact that antibodies to S1 also reacted directly with HP-6 in three out of four mice although one was a low responder. The M2 peptide also induced low levels of antibody to HP-6 in three out of four mice. Sero conversions also occurred following the second immunization with the S1 and M1 multimeric peptides.

Since the responses to the polyclonal pooled anti-IgM, IgA and IgG conjugated antibodies were lower than expected, the mouse serums harvested from mice five weeks after the second immunization were tested, when sufficient amounts were available, in an ELISA using conjugated affinity purified anti-IgG. Table 10 shows the IgG antibody response of individual mice to the indicated multimer. It can be noted that many of the antibody responses were very high, e.g., greater than 1.0, and some were greater than 2, when the S1 peptide was used as immunogen in the presence of FCA or FIA. This indicates that significant amounts of IgG antibody were induced in mice, even when the peptides were given in Freund's incomplete adjuvant The fact that the antibodies cross-reacted with peptides with different linkers, but the same HP-6 sequence (doubly underlined values), shows that the antibodies detected are directed against the HP-6 moiety. The ability to induce high levels of IgG antibodies also indicates that the multimers are able to induce memory cells. Thus the multimer-induced immune response is long term.

Tables 11 and 12 show summaries of the proportion of mice mounting an antibody response to individual multimers inoculated in Freund's complete (FCA) or incomplete adjuvant (FIA) five weeks after one immunization (Table 10) and five weeks after a second immunization (Table 11).

TABLE 11

Summary of Proportion of ICR mice with antibody to peptides and linkers five weeks after immunization with peptides.

| Peptide | S1 FCA[a] | S1 FIA[b] | S2 FCA | S2 FIA | M1 FCA | M1 FIA | M2 FCA | M2 FIA | M2 FCA | M2 FIA | M2 FCA | B3 FIA |
|---|---|---|---|---|---|---|---|---|---|---|---|---|
| S1     | 2/3 | 2/3 | 0/3 | 0/0 | 1/3 | 2/3 | 0/3 | ND  | 0/3 | ND  | 0/2 | ND  |
| HP-6   | 2/3 | 1/3 | 2/3 | 0/3 | 2/3 | 0/3 | 1/3 | 0/3 | 1/3 | 0/3 | 0/3 | 0/3 |
| S2 20  | 1/3 | 0/3 | 0/3 | 0/3 | 1/3 | 0/3 | 1/3 | 0/3 | 0/3 | 0/3 | 0/3 | 0/3 |
| S2 22  | 2/3 | 0/3 | 0/3 | 0/3 | 0/3 | 0/3 | 0/3 | 0/3 | 0/3 | 0/3 | 0/3 | 0/3 |
| S1 LL  | 0/0 | 0/1 | ND  | ND  |     |     |     |     |     |     |     |     |
| S1 RL  | 0/0 | 0/1 | ND  | ND  |     |     |     |     |     |     |     |     |
| S2     | 1/3 | 1/2 | 0/3 | ND  | 2/3 | 2/3 | 1/3 | ND  | 0/3 | ND  | 0/2 | ND  |
| S2 LL  | 0/0 | 0/2 | ND  | ND  |     |     |     |     |     |     |     |     |
| S2 RL  | 0/0 | 0/2 | ND  | ND  |     |     |     |     |     |     |     |     |
| M1     | 0/3 | 1/2 | 0/3 | ND  | 2/3 | 3/3 | 1/3 | ND  | 0/3 | ND  | 0/2 | ND  |
| M1 LL  | —   | —   | —   | —   | 0/1 | 1/3 | 0/0 | 0/0 | 0/0 | 0/0 | —   | —   |
| M1 RL  | —   | —   | —   | —   | 0/1 | 0/2 | 0/1 | 0/3 | 0/0 | 0/0 | —   | —   |
| M2     | 0/3 | 0/2 | 0/3 | ND  | 0/3 | 0/3 | 1/3 | ND  | 0/3 | ND  | 0/2 | ND  |
| M2 LL  | —   | —   | —   | —   | 0/0 | 1/2 | 0/0 | 0/0 | 0/0 | 0/0 | —   | —   |
| M2 RL  | —   | —   | —   | —   | 0/1 | 0/1 | 1/1 | 1/1 | 1/1 | ND  | —   | —   |
| M2-B2  |     |     |     |     |     |     |     |     | 0/3 | 0/3 |     |     |
| M2-B3  |     |     |     |     |     |     |     |     |     |     | 0/3 | 0/3 |

[a] = Freund's complete adjuvant
[b] = Freund's incomplete adjuvant

TABLE 12

Summary of Proportion of ICR mice with antibody to peptides and linkers five weeks after second immunization with peptides.

| Peptide | S1 FCA[a] | S1 FIA[b] | S2 FCA | S2 FIA | M1 FCA | M1 FIA | M2 FCA | M2 FIA | M2B2 FCA | M2B2 FIA | M2B3 FCA | M2B3 FIA |
|---|---|---|---|---|---|---|---|---|---|---|---|---|
| S1    | 3/3 | 2/2 | 0/3 | 0/3 | 1/3 | 2/3 | 0/3 | 1/2 | 1/3 | 0/3 | 0/3 | 0/3 |
| HP-6  | 2/3 | 1/2 | 0/3 | 2/3 | 2/3 | 0/3 | 1/3 | 1/2 | 0/3 | 0/3 | 0/3 | 0/3 |
| S1 LL | 0/3 | 0/2 | 0/3 | 0/3 | —   | —   | —   | —   | —   | —   | —   | —   |
| S1 RL | 1/3 | 0/2 | 0/3 | 0/3 | —   | —   | —   | —   | —   | —   | —   | —   |
| S2    | 1/3 | 1/2 | 0/3 | 0/3 | 0/3 | 1/3 | 1/3 | 2/2 | 2/3 | 0/3 | 0/3 | 0/3 |
| S2 LL | 1/3 | 0/2 | 0/3 | 0/3 | —   | —   | —   | —   | —   | —   | —   | —   |
| S2 RL | 1/3 | 0/2 | 0/3 | 0/3 | —   | —   | —   | —   | —   | —   | —   | —   |
| M1    | 1/3 | 1/2 | 0/3 | 0/3 | 2/3 | 3/3 | 1/3 | 2/2 | 1/3 | 0/3 | 0/3 | 0/3 |

TABLE 12-continued

Summary of Proportion of ICR mice with antibody to peptides and linkers five weeks after second immunization with peptides.

| Peptide | S1 FCA[a] | S1 FIA[b] | S2 FCA | S2 FIA | M1 FCA | M1 FIA | M2 FCA | M2 FIA | M2B2 FCA | M2B2 FIA | M2B3 FCA | M2B3 FIA |
|---|---|---|---|---|---|---|---|---|---|---|---|---|
| M1 LL |  |  | 0/2 | 0/1 | <u>1/2</u> | 0/2 |  |  |  |  |  |  |
| M1 RL |  |  | 0/2 | 0/1 | 0/2 | 0/2 |  |  |  |  |  |  |
| M2 | <u>1/3</u> | 0/2 | 0/3 | 0/3 | 0/3 | 0/3 | <u>1/3</u> | <u>1/3</u> | 0/3 | 0/3 | 0/3 | 0/3 |
| M2 LL |  |  | 0/2 | 0/1 | 1/2 | 0/2 |  |  |  |  |  |  |
| M2 RL |  |  | 0/2 | 0/1 | 1/2 | 0/2 |  |  |  |  |  |  |

FCA = Freund's complete adjuvant
FIA = Freund's incomplete adjuvant

It can be noted that the largest proportion of positive mice correspond to those mice inoculated with multimers that induced the highest levels of antibody. Thus, certain multimers can induce high levels of antibody in a high proportion of mice.

Overall the data illustrate that certain multimeric peptides are able to induce high levels of antibody, including IgG antibody, in the absence of complete adjuvant and with as few as two immunizations. The fact that the antibody cross-reacts with unrelated multimers containing the same epitope as the immunogen indicates that the antibody detected was specific. This conclusion is supported by the ability of the antibodies in some of the mice to react directly with the HP-6 epitope.

EXAMPLE 8

Generic construction of Linking Biologically Active Peptides

In general to ensure initial success the peptides should be fashioned similar to the S1 and S2 or M1 and M2 peptides described herein. But it is possible to use modifications, especially in regard to the length of the linkers, but the efficacy needs to be determined empirically. An amphipathic epitope should be selected for the antigen of interest, however other linear sequences have not been ruled out. The linkers should consist of 12 amino acid residues of alternating hydropathicity, but shorter linkers may serve as well. The linkers of biologically active multimers are generally composed of alternating hydrophobic and hydrophilic amino acids as indicated in the S1 and S2 type peptides, but more neutral spacing amino acids may be used that would allow for various kinds of folding resulting in different activities, as indicated by the different activities of the multimers extracted from the gel bands for the M1 and M2 peptides. In fact, one may use naturally occurring amino acid sequences with similar alternating patterns to get linked monomers with biological activity as indicated in the M1 peptide. Linkage can be checked by neutral polyacrylamide gel electrophoreses. Depending on the desired biological activity needed, bands may be most effectively eluted from gels using 10 to 100% DMSO followed by dilution in Tris-HCl. It is likely that molecular sizing columns could also be used, because of the stability of the multimers. The stock multimers are also very active for different biological functions and thus could be diluted and used neat as desired. The peptides may be synthesized, for example, by the following method:

Peptides described herein were synthesized in the laboratory of Dr. H. M. Johnson on a Biosearch Model 9500AT automated peptide synthesizer (Millipore Corporation, Bedford, Mass.) using $N^{\alpha}$-((-fluoroenyl)methyloxycarbonyl chemistry (Chang et al.). Peptides were cleaved from the resins using trifluoroacetic acid/ethanedithiol/thioanisole/anisole at a ratio of 90/3/5/2. The cleaved peptides were then extracted in ether and ethyl acetate and subsequently dissolved in water and lyophilized. Reverse phase HPLC analysis of the crude peptides revealed one major peak in each profile, hence additional purification was not warranted. Amino acid analyses of the peptides showed that the amino acid composition corresponded closely to theoretical values and indicated a purity of greater than 90%. Table 13 shows a typical amino acid analysis.

TABLE 13

Typical Amino Acid Analysis

| Amino Acid | Notes | Range (± 10%) | Rationale |
|---|---|---|---|
| Cys-acid | 1,2 | 1.00 |  |
| Asx |  | 1.00 |  |
| Thr |  | 1.00 |  |
| Ser |  | 0.80 | dehydration |
| Glx |  | 1.00 |  |
| Gly |  | 1.25 | from degradation of other aa |
| Ala | 3 | 1.00 |  |
| Val |  | 0.90 | rearrangement |
| Met |  | 0.7 | S-alkylation, oxidation |
| Ile |  | 0.85 | rearrangement |
| Leu | 3 | 1.00 |  |
| Tyr | 1 | 1.00 |  |
| Phe | 2 | 1.00 |  |
| His | 2 | 0.700–1.40 | oxidation |
| Lys | 2 | 1.00 |  |
| Trp | 1,2 | 0.500–1.00 | very unstable |
| Arg | 2 | 1.00 |  |
| Pro |  | 1.15–1.18 |  |

Notes:
1. Detection requires special hydrolysis
2. Frequently difficult to quantitate
3. Extremely stable Table 14 shows amino acid analyses of inventive peptides synthesized.

TABLE 14

| Peptide | Amino Acid | Theoretical | Actual |
|---|---|---|---|
| S1 | Asx | 4 | 4.3 |
|  | Ser | 4 | 4.2 |
|  | Glx | 5 | 5.1 |
|  | Ala | 4 | 4.4 |
|  | Val | 2 | 1.7 |
|  | Ile | 7 | 6.3 |
|  | Leu | 3 | 3.0 |

TABLE 14-continued

| Peptide | Amino Acid | Theoretical | Actual |
|---|---|---|---|
| | Tyr | 2 | 2.2 |
| | His | 2 | 1.4 |
| | Lys | 1 | 0.9 |
| | Trp | 1 | — |
| | Arg | 2 | 2.1 |
| S2 | Asx | 5 | 4.6 |
| | Ser | 2 | 2.0 |
| | Glx | 4 | 4.5 |
| | Gly | 2 | 2.5 |
| | Ala | 2 | 2.1 |
| | Val | 2 | 2.0 |
| | Ile | 2 | 1.4 |
| | Leu | 6 | 6.3 |
| | Tyr | 3 | 3.2 |
| | Phe | 2 | 2.2 |
| | His | 3 | 3.0 |
| | Lys | 1 | 1.2 |
| | Trp | 1 | — |
| | Arg | 2 | 2.0 |
| M1 | Asx | 2 | 2.1 |
| | Thr | 1 | 0.8 |
| | Ser | 6 | 5.5 |
| | Glx | 4 | 4.3 |
| | Ala | 4 | 4.6 |
| | Val | 2 | 2.3 |
| | Ile | 5 | 4.2 |
| | Leu | 3 | 3.1 |
| | His | 4 | 4.4 |
| | Trp | 1 | — |
| | Arg | 3 | 3.4 |
| M2 | Asx | 5 | 5.1 |
| | Thr | 1 | 1.0 |
| | Ser | 4 | 3.7 |
| | GLX | 4 | 4.5 |
| | Ala | 2 | 2.2 |
| | Val | 2 | 2.3 |
| | Ile | 2 | 1.3 |
| | Leu | 4 | 3.8 |
| | His | 2 | 1.6 |
| | Trp | 1 | — |
| | Arg | 5 | 5.1 |
| | Tyr | 1 | 1.4 |

REFERENCES

The following references, to the extent that they provide exemplary procedural or other details supplementary to those set forth herein, are specifically incorporated herein by reference.

Blalock et al., *Biochem. Biophys. Res. Comm.*, 121:203–207, 1984.

Bost et al., *Proc. Natl. Acad. Sci.*, 82:1372–1375, 1985.

Chang et al., "Solid-phase peptide synthesis using mild base cleavage of $N^{\alpha}$-(-fluoroenyl)methyloxycarbonyl amino acids, exemplified by a synthesis of dihydrosomatostatin," *Int. J. Pept. Protein Res.*, 11:246, 1978.

Goodman, J. W., "Immunogenicity and Antigenic Specificity", *Basic and Clinical Immunology,* edited by D. P. Stites and A. I. Terr., Appleton and Lange, Norwalk, Conn. pp. 101–108, 1991.

Guillet, et al., *Science,* 235:865–870, 1987.

Hale et al., *International Immunology* 1:409–415, 1989.

Kyte and Doolittle, *J. Mol. Biol.,* 157: 105–132, 1982.

Merrifield, R., *J. Am. Chem. Soc.* 85:2149, 1963.

Sette, et al., *J. Immunol.* 142:35–40, 1988.

Tam et al., *Proc. Natl. Acad. Sci.,* 85:5409–5413, 1988.

U.S. Pat. No. 3,791,932.
U.S. Pat. No. 3,949,064.
U.S. Pat. No. 4,174,384.
U.S. Pat. No. 4,578,770.
U.S. Pat. No. 4,596,792.
U.S. Pat. No. 4,599,230.
U.S. Pat. No. 4,599,231.
U.S. Pat. No. 4,601,903.
U.S. Pat. No. 4,608,251.
U.S. Pat. No. 5,077,195.

What is claimed is:

1. A non-covalently interlinked multimer comprising monomers (A)-Ag-(a) and (B)-Ag-(b), wherein Ag is an HP-6 epitope; and A, a, B, and b are independently peptide linkers of about 3 to 12 amino acids covalently bound to the antigenic epitope; wherein peptide linker A has binding affinity for peptide linker b and peptide linker a has binding affinity for peptide linker B due to a pattern of alternating hydrophilic and hydrophobic amino acids or groups of amino acids.

2. The multimer of claim 1 wherein A and B are the same linker and a and b are the same linker.

3. The multimer of claim 1 wherein the pattern is of singly alternating hydrophilic and hydrophobic amino acid.

4. The multimer of claim 1 wherein the groups of amino acids include 2 or 3 amino acids.

5. The multimer of claim 1 wherein A and a are selected from the group consisting of S1-L (SEQ ID NO:6) and S1-R (SEQ ID NO:7), S2-L (SEQ ID NO:8) and S2-R (SEQ ID NO:9), M1-L(SEQ ID NO:1) and M1-R (SEQ ID NO:3), M2-L (SEQ ID NO:4) and M2-R (SEQ ID NO:5), S20-L (SEQ ID NO:10) and S20-R (Gly-Leu-Gln), S22-L (SEQ ID NO:11) and S22-R (SEQ ID NO:12).

6. The multimer of claim 1 wherein B and b are selected from the group consisting of S1-L (SEQ ID NO:6) and S1-R (SEQ ID NO:7), S2-L (SEQ ID NO:8) and S2-R (SEQ ID NO:9), M1-L(SEQ ID NO:1) and M1-R (SEQ ID NO:3), M2-L (SEQ ID NO:4) and M2-R (SEQ ID NO:5), S20-L (SEQ ID NO:10) and S20-R (Gly-Leu-Gln), S22-L (SEQ ID NO:11) and S22-R (SEQ ID NO:12).

7. The multimer of claim 1 wherein the peptide linkers have spacer amino acids.

8. A non-covalently interlinked multimer made by a process comprising the step of incubating a first monomer, (A)-Ag-(a), with a second monomer, (B)-Ag-(b), under conditions facilitating peptide interactions to form a non-covalently interlinked multimer, wherein Ag is an HP-6 epitope; and A, a, B, and b are independently peptide linkers of about 3 to 12 amino acids; wherein peptide linker A has non-covalent binding affinity for peptide linker b and peptide linker a has non-covalent binding affinity for peptide linker B due to a pattern of alternating hydrophilic and hydrophobic amino acids or groups of amino acids.

9. The multimer of claim 8 wherein the conditions facilitate dissolution of the monomers in a physiologically acceptable aqueous solvent.

10. A method of producing a non-covalently interlinked multimer comprising the step of incubating a first monomer, (A)-Ag-(a), with a second monomer, (B)-Ag-(b), under conditions facilitating peptide interactions to form a non-covalently interlinked multimer, wherein Ag is an HP-6 epitope; and A, a, B, and b are independently peptide linkers of about 3 to 12 amino acids; wherein peptide linker A has non-covalent binding affinity for peptide linker b and peptide linker a has binding affinity for peptide linker B due to a pattern of alternating hydrophilic and hydrophobic amino acids or groups of amino acids.

11. The method of claim 10 wherein the conditions facilitate dissolution of the monomers of the multimer in a physiologically acceptable aqueous solvent.

12. A method of producing an antibody having specific binding affinity for the non-covalently linked multimer of claim 1 in an animal, the method comprising the steps of obtaining an animal capable of producing antibody and injecting into the animal the non-covalently interlinked multimer.

13. The method of claim 12 further comprising the step of recovering the antibody from biological fluid of the animal.

* * * * *